(12) United States Patent
Martin et al.

(10) Patent No.: US 10,377,801 B2
(45) Date of Patent: Aug. 13, 2019

(54) AMELIORATION OF CHRONIC KIDNEY DISEASE

(71) Applicant: Northwestern University, Evanston, IL (US)

(72) Inventors: Aline C. Martin, Chicago, IL (US); Nicolae V. David, Chicago, IL (US); Myles S. Wolf, Winnetak, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/342,678

(22) Filed: Nov. 3, 2016

(65) Prior Publication Data

US 2017/0121382 A1 May 4, 2017

Related U.S. Application Data

(60) Provisional application No. 62/250,863, filed on Nov. 4, 2015.

(51) Int. Cl.
| A61K 38/00 | (2006.01) |
| C07K 14/47 | (2006.01) |
| C07K 14/50 | (2006.01) |

(52) U.S. Cl.
CPC .......... *C07K 14/473* (2013.01); *A61K 38/00* (2013.01); *C07K 14/50* (2013.01)

(58) Field of Classification Search
None
See application file for complete search history.

(56) References Cited

U.S. PATENT DOCUMENTS

| 5,139,941 | A | 8/1992 | Muzyczka et al. |
| 5,173,414 | A | 12/1992 | Lebkowski et al. |
| 5,676,954 | A | 10/1997 | Brigham |
| 5,824,544 | A | 10/1998 | Armentano et al. |
| 5,830,730 | A | 11/1998 | German et al. |
| 5,843,742 | A | 12/1998 | Natsoulis et al. |
| 5,872,154 | A | 2/1999 | Wilson et al. |
| 5,885,808 | A | 3/1999 | Spooner et al. |
| 5,908,777 | A | 6/1999 | Lee et al. |
| 5,981,225 | A | 11/1999 | Kochanek et al. |
| 5,994,106 | A | 11/1999 | Kovesdi et al. |
| 5,994,128 | A | 11/1999 | Fallaux et al. |
| 5,994,132 | A | 11/1999 | Chamberlain et al. |
| 6,001,557 | A | 12/1999 | Wilson et al. |
| 6,019,978 | A | 2/2000 | Ertl et al. |
| 6,033,908 | A | 3/2000 | Bout et al. |
| 6,057,158 | A | 5/2000 | Chamberlain et al. |
| 6,063,622 | A | 5/2000 | Chamberlain et al. |
| 6,083,750 | A | 7/2000 | Chamberlain et al. |
| 6,451,596 | B1 | 9/2002 | Chamberlain et al. |
| 6,995,018 | B1 * | 2/2006 | Fisher .............. G01N 33/57484 435/7.1 |

FOREIGN PATENT DOCUMENTS

| WO | WO 92/01070 | 1/1992 |
| WO | WO 93/03769 | 3/1993 |
| WO | WO 99/02685 | 1/1999 |
| WO | WO 00/09575 | 2/2000 |
| WO | WO 00/12738 | 3/2000 |

OTHER PUBLICATIONS

Kempf et al. (2006, Cir. Res. 98:351-350).*
Tokuriki et al., 2009, Curr. Opin. Struc. Biol. 19:596-604.*
Bhattacharya et al. (2017, PLoS ONE 12(3): e0171355, https://doi.org/10.1371/journal.pone.0171355).*
Srinivasan et al. (1999, Connective Tissue Research 40:251-258).*
Toyosawa et al. (2004, Modern Pathology 17:573-578).*
Becker et al., Use of Recombinant Adenovirus for Metabolic Engineering of Mammalian Cells. Methods Cell Biol. 1994;43 Pt A:161-89.
Carter, Adeno-associated virus vectors. Curr Opin Biotechnol. Oct. 1992;3(5):533-9.
Felgner et al., Cationic liposome-mediated transfection. Nature. Jan. 26, 1989;337(6205):387-8.
Felgner et al.,Lipofection: a highly efficient, lipid-mediated DNA-transfection procedure. Proc Natl Acad Sci U S A. Nov. 1987;84(21):7413-7.
Ferrari et al., New developments in the generation of Ad-free, high-titer rAAV gene therapy vectors. Nat Med. Nov. 1997;3(11):1295-7.
Graham et al., Manipulation of adenovirus vectors. Methods Mol Biol. 1991;7:109-28.
Gregorevic et al., Systemic delivery of genes to striated muscles using adeno-associated viral vectors. Nat Med. Aug. 2004;10(8):828-34.
Haft et al., A guild of 45 CRISPR-associated (Cas) protein families and multiple CRISPR/Cas subtypes exist in prokaryotic genomes. PLoS Comput Biol. Nov. 2005;1(6):e60.
Hug, Liposomes for the transformation of eukaryotic cells. Biochim Biophys Acta. Jul. 26, 1991;1097(1):1-17.
Qi et al., γ-Secretase inhibition of murine choroidal neovascularization is associated with reduction of superoxide and proinflammatory cytokines. Invest Ophthalmol Vis Sci. Feb. 1, 2012;53(2):574-85.
Jansen et al., Identification of genes that are associated with DNA repeats in prokaryotes. Mol Microbiol. Mar. 2002;43(6):1565-75.
Kotin,Prospects for the use of adeno-associated virus as a vector for human gene therapy. Hum Gene Ther. Jul. 1994;5(7):793-801.
Lebkowski et al., Adeno-associated virus: a vector system for efficient introduction and integration of DNA into a variety of mammalian cell types. Mol Cell Biol. Oct. 1988;8(10):3988-96.
Makarova et al., A DNA repair system specific for thermophilic Archaea and bacteria predicted by genomic context analysis. Nucleic Acids Res. Jan. 15, 2002;30(2):482-96.
Makarova et al., A putative RNA-interference-based immune system in prokaryotes: computational analysis of the predicted enzymatic machinery, functional analogies with eukaryotic RNAi, and hypothetical mechanisms of action. Biol Direct. Mar. 16, 2006;1:7.

(Continued)

*Primary Examiner* — Elizabeth C. Kemmerer
(74) *Attorney, Agent, or Firm* — Casimir Jones, S.C.; David W. Staple

(57) ABSTRACT

Provided herein are compositions and methods for the treatment of Chronic Kidney Disease (CKD) and/or the amelioration or prevention of symptoms, conditions and diseases associated therewith.

2 Claims, 26 Drawing Sheets

Specification includes a Sequence Listing.

(56) References Cited

OTHER PUBLICATIONS

Muzyczka, Use of adeno-associated virus as a general transduction vector for mammalian cells. Curr Top Microbiol Immunol. 1992;158:97-129.
Shelling et al., Targeted integration of transfected and infected adeno-associated virus vectors containing the neomycin resistance gene. Gene Ther. May 1994;1(3):165-9.
Straubinger et al., Liposomes as carriers for intracellular delivery of nucleic acids. Methods of Enzymology. 1983;101:512-527.
Westfall et al., Chapter 15 Adenovirus—Mediated Myofilament Gene Transfer into Adult Cardiac Myocytes. Meth Cell Biol. 1997;52:307-322.
Zhou et al., Adeno-associated virus 2-mediated high efficiency gene transfer into immature and mature subsets of hematopoietic progenitor cells in human umbilical cord blood. J Exp Med. Jun. 1, 1994;179(6):1867-75.

* cited by examiner

FIG. 4A
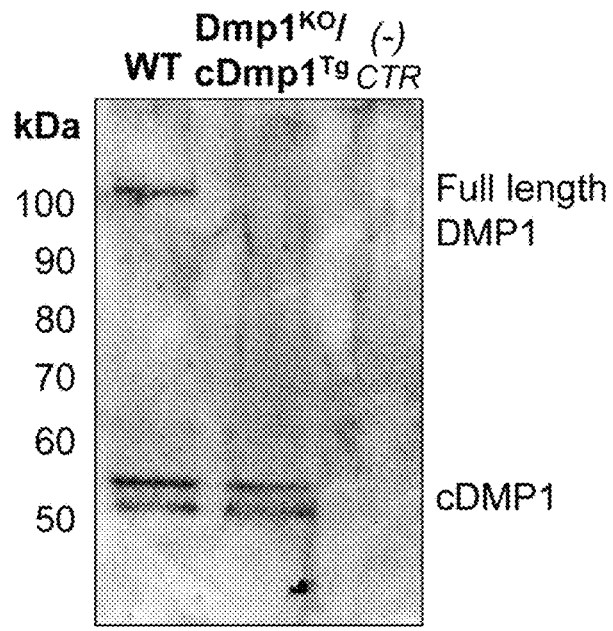
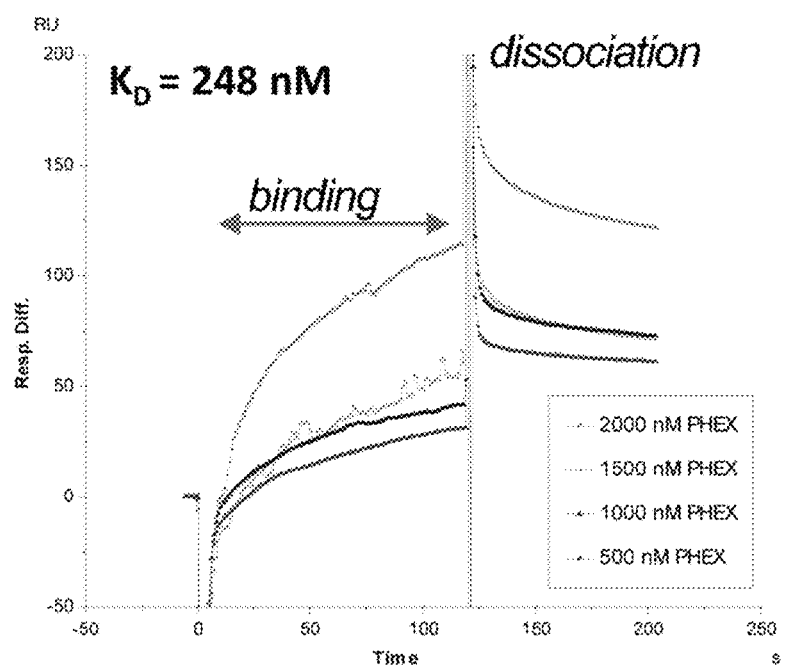
FIG. 4B

FIG. 12A
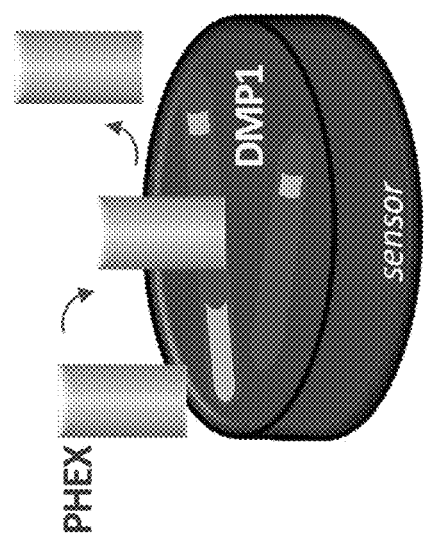
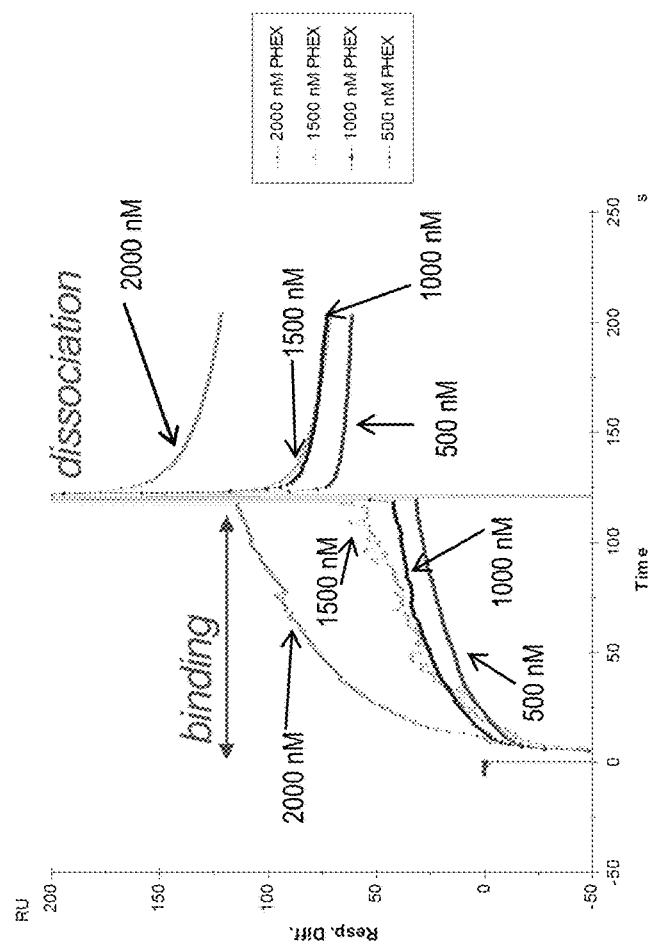

```
                          SEQUENCE LISTING

<160> NUMBER OF SEQ ID NOS: 3

<210> SEQ ID NO 1
<211> LENGTH: 503
<212> TYPE: PRT
<213> ORGANISM: Mus musculus

<400> SEQUENCE: 1

Met Lys Thr Val Ile Leu Leu Val Phe Leu Trp Gly Leu Ser Cys Ala
1               5                   10                  15

Leu Pro Val Ala Arg Tyr His Asn Thr Glu Ser Glu Ser Ser Glu Glu
            20                  25                  30

Arg Thr Gly Asp Leu Ala Gly Ser Pro Pro Pro Thr Asn Ser Glu
        35                  40                  45

Ser Ser Glu Glu Ser Gln Ala Ser Pro Glu Gly Gln Ala Asn Ser Asp
    50                  55                  60

His Thr Asp Ser Ser Glu Ser Gly Glu Glu Leu Gly Tyr Asp Arg Gly
65                  70                  75                  80

Gln Tyr Arg Pro Ala Gly Gly Leu Ser Lys Ser Thr Gly Thr Gly Ala
                85                  90                  95

Asp Lys Glu Asp Asp Glu Asp Ser Gly Asp Thr Phe Gly Asp
            100                 105                 110

Glu Asp Asn Asp Leu Gly Pro Glu Glu Gly Gln Trp Gly Gly Pro Ser
        115                 120                 125

Lys Leu Asp Ser Asp Glu Asp Ser Thr Asp Thr Thr Gln Ser Ser Glu
130                 135                 140

Asp Ser Thr Ser Gln Glu Asn Ser Ala Gln Asp Thr Pro Ser Asp Ser
145                 150                 155                 160

Lys Asp His Asp Ser Glu Asp Glu Ala Asp Ser Arg Pro Glu Ala Gly
            165                 170                 175

Asp Ser Thr Gln Asp Ser Glu Ser Glu Glu Arg Val Gly Gly Gly
        180                 185                 190

Ser Glu Gly Glu Ser Ser His Gly Asp Gly Ser Glu Phe Asp Asp Glu
    195                 200                 205

Gly Met Gln Ser Asp Asp Pro Glu Ser Thr Arg Ser Asp Arg Gly His
210                 215                 220

Ala Arg Met Ser Ser Ala Gly Ile Arg Ser Glu Glu Ser Lys Gly Asp
225                 230                 235                 240

His Glu Pro Thr Ser Thr Gln Asp Ser Asp Asp Ser Gln Ser Val Glu
            245                 250                 255

Phe Ser Ser Arg Lys Ser Phe Arg Arg Ser His Val Ser Glu Glu Asp
        260                 265                 270

Tyr Arg Gly Glu Leu Thr Asp Ser Asn Ser Arg Glu Thr Gln Ser Asp
    275                 280                 285

Ser Thr Glu Asp Thr Ala Ser Lys Glu Glu Ser Arg Ser Glu Ser Gln
290                 295                 300

Glu Asp Thr Ala Glu Ser Gln Ser Gln Glu Asp Ser Pro Glu Gly Gln
305                 310                 315                 320

Asp Pro Ser Ser Glu Ser Ser Glu Glu Ala Gly Glu Pro Ser Gln Glu
```

```
            325                 330                 335
Ser Ser Ser Glu Ser Gln Glu Gly Val Thr Ser Glu Ser Arg Gly Asp
        340                 345                 350

Asn Pro Asp Asn Thr Ser Gln Ala Gly Asp Gln Glu Asp Ser Glu Ser
            355                 360                 365

Ser Glu Glu Asp Ser Leu Asn Thr Phe Ser Ser Glu Ser Gln Ser
        370                 375                 380

Thr Glu Glu Gln Ala Asp Ser Glu Ser Asn Glu Ser Leu Ser Leu Ser
385                 390                 395                 400

Glu Glu Ser Gln Glu Ser Ala Gln Asp Gly Asp Ser Ser Gln Glu
            405                 410                 415

Gly Leu Gln Ser Gln Ser Ala Ser Thr Glu Ser Arg Ser Gln Glu Ser
            420                 425                 430

Gln Ser Glu Gln Asp Ser Arg Ser Glu Glu Asp Ser Asp Ser Gln Asp
            435                 440                 445

Ser Ser Arg Ser Lys Glu Glu Ser Asn Ser Thr Gly Ser Ala Ser Ser
450                 455                 460

Ser Glu Glu Asp Ile Arg Pro Lys Asn Met Glu Ala Asp Ser Arg Lys
465                 470                 475                 480

Leu Ile Val Asp Ala Tyr His Asn Lys Pro Ile Gly Asp Gln Asp Asp
            485                 490                 495

Asn Asp Cys Gln Asp Gly Tyr
        500

<210> SEQ ID NO 2
<211> LENGTH: 298
<212> TYPE: PRT
<213> ORGANISM: Mus musculus

<400> SEQUENCE: 2

Asp Asp Glu Gly Met Gln Ser Asp Asp Pro Glu Ser Thr Arg Ser Asp
1               5                   10                  15

Arg Gly His Ala Arg Met Ser Ser Ala Gly Ile Arg Ser Glu Glu Ser
            20                  25                  30

Lys Gly Asp His Glu Pro Thr Ser Thr Gln Asp Ser Asp Ser Gln
        35                  40                  45

Ser Val Glu Phe Ser Ser Arg Lys Ser Phe Arg Arg Ser His Val Ser
    50                  55                  60

Glu Glu Asp Tyr Arg Gly Glu Leu Thr Asp Ser Asn Ser Arg Glu Thr
65                  70                  75                  80

Gln Ser Asp Ser Thr Glu Asp Thr Ala Ser Lys Glu Glu Ser Arg Ser
                85                  90                  95

Glu Ser Gln Glu Asp Thr Ala Glu Ser Gln Ser Gln Glu Asp Ser Pro
            100                 105                 110

Glu Gly Gln Asp Pro Ser Ser Glu Ser Ser Glu Glu Ala Gly Glu Pro
        115                 120                 125

Ser Gln Glu Ser Ser Ser Glu Ser Gln Glu Gly Val Thr Ser Glu Ser
    130                 135                 140

Arg Gly Asp Asn Pro Asp Asn Thr Ser Gln Ala Gly Asp Gln Glu Asp
145                 150                 155                 160

Ser Glu Ser Ser Glu Glu Asp Ser Leu Asn Thr Phe Ser Ser Ser Glu
                165                 170                 175

Ser Gln Ser Thr Glu Glu Gln Ala Asp Ser Glu Ser Asn Glu Ser Leu
            180                 185                 190
```

```
Ser Leu Ser Glu Glu Ser Gln Glu Ser Ala Gln Asp Gly Asp Ser Ser
            195                 200                 205
Ser Gln Glu Gly Leu Gln Ser Gln Ser Ala Ser Thr Glu Ser Arg Ser
    210                 215                 220
Gln Glu Ser Gln Ser Glu Gln Asp Ser Arg Ser Glu Glu Asp Ser Asp
225                 230                 235                 240
Ser Gln Asp Ser Ser Arg Ser Lys Glu Glu Ser Asn Ser Thr Gly Ser
                245                 250                 255
Ala Ser Ser Glu Glu Asp Ile Arg Pro Lys Asn Met Glu Ala Asp
            260                 265                 270
Ser Arg Lys Leu Ile Val Asp Ala Tyr His Asn Lys Pro Ile Gly Asp
        275                 280                 285
Gln Asp Asp Asn Asp Cys Gln Asp Gly Tyr
    290                 295

<210> SEQ ID NO 3
<211> LENGTH: 2754
<212> TYPE: DNA
<213> ORGANISM: Mus musculus

<400> SEQUENCE: 3
cagctggaga  gtggcttctc  tgagatccct  cttcgagaac  ttcgctgagg  ttttgacctt      60
gtgggaaaaa  gaccttggga  gccagagagg  gtagaggaat  cgcatcccaa  tatgaagact     120
gtcattctcc  ttgtgttcct  ttgggggctg  tcctgtgctc  tcccagttgc  cagataccac     180
aatactgaat  ctgaaagctc  tgaagagagg  acgggtgatt  tggctgggtc  accaccacca     240
cccacgaaca  gtgagtcatc  agaagaaagt  caagctagcc  cagagggaca  ggcaaatagt     300
gaccacacgg  acagcagtga  atctggagag  gagctgggct  acgacagagg  ccagtacaga     360
ccggctggtg  gactctctaa  gagtacgggg  accggcgccg  ataaggagga  tgatgaagac     420
gacagtggag  atgatacctt  tggcgatgag  gacaatgatc  tagggcccga  agaaggacag     480
tggggaggac  cctccaaact  ggacagtgat  gaggactcca  cagacaccac  acagtccagt     540
gaagacagca  cctctcaaga  aaacagtgcc  aagataccc   ccagcgacag  caaagaccac     600
gacagtgagg  atgaggcaga  cagccggcct  gaggcaggcg  actccactca  ggacagtgag     660
agtgaggaac  agcgggtggg  aagtggcagc  gaggggaga   gtagccacgg  ggacggttct     720
gagttcgatg  atgaagggat  gcagagcgac  gaccccgaga  gtaccaggag  cgatcgaggc     780
cacgccagaa  tgagcagcgc  tggtatcagg  tcggaagaat  ctaaagggga  ccacgagccc     840
acgagcactc  aggattcaga  tgacagccag  tctgtggaat  tttcaagcag  gaagtccttc     900
agaaggtccc  acgtctctga  ggaagactac  agaggtgagc  ttactgacag  caacagcagg     960
gaaacccaga  gcgactccac  ggaggatacg  gcctccaagg  aggaaagcag  gagcgagtct    1020
caggaggaca  cagccgagag  ccagtcccag  gaagatagcc  cagaggggca  gacccccagc    1080
agtgagtcca  gcgaagaggc  tggtgagcca  tcccaggaaa  gcagcagcga  atctcaggaa    1140
ggggtgacca  gcgagtccag  gggtgacaac  ccagataaca  caagtcaggc  aggagaccaa    1200
gaagacagtg  agtccagtga  ggaggacagc  ctgaacacat  ctccagctc   agaaagccag    1260
tccaccgaga  gcaagctgaa  cagcgagtcc  aacgagagcc  tcagcctctc  cgaggagagt    1320
caggagtcgg  cccaggatgg  tgacagctcc  agccaggaag  gcctgcagtc  ccagagcgca    1380
tccactgaga  gcaggagcca  ggagagccag  tctgagcagg  acagccgttc  tgaggaagac    1440
agtgactctc  aggacagtag  ccgatccaaa  gaagagagca  actccacagg  gagcgcttcc    1500
```

```
                                        -continued
agcagcgagg aggacatccg tcccaagaac atggaagctg acagtaggaa actaatagtt    1560
gatgcttacc acaacaaacc catcggggac caagatgaca atgactgtca ggacggctac    1620
tagcattagc ttgtctaaga aatggctctc acaggacgga gtcttggggg ctccagagta    1680
gagagttcac tataactata atttattaat gttttggtca gaaggagaac caggggcagg    1740 ttttttttgtt ttgttttgtt tttgtttgtt tgtttgtttt ccccctgtga ggaactgttg    1800
gacacgacac tgttttccag ggtgtctccc actccttaga ggcttaagta cgtgggatga    1860
tgtcagagca cacatggtga gagaagaaca cagggatcac gtgcacagcc gcttcacaga    1920
tgctctggtt caccaacctg acagtgactg aggttctggt acacaccagg cacagccctg    1980
ggcgggggag ggggtggtgg tgcttcaggc tcagttttgc tccggaggag cttgttccaa    2040
ggagactctc aaaagtaaca cattaaagga tacaaagaag gagccctgg  agctgggcta    2100 cattgctttg gctcctggag ggtgagaact tactgcagca agccctgcc  gcagctgagg    2160 cgagtaccac agggaatggg agcaggacag gaagtgacca gttttgcttt ggagaatcag    2220
aggttccaca gtagcaaagc ctggagctgg agggttacat aggatttctc cattgaagac    2280
aatataactc tatttattct tgagataagc agtatcaaat cgtatgcaat taaatattta    2340
gtacgtaaag gcattctcaa atgataaccc aatgggatat cttggataac atatttttcc    2400
caacgaattt accttattga gtgcttttgt gggccttctg taaacatggc ctcaatgatg    2460
aggaggagga agaaaatttg gtgtggagat gggagaaaaa cataattaaa agaagattta    2520
tagcttaatt ttttccaga ttatttatgt gcagtgtaaa tactatccct gagtcctttc    2580
tatgtgttgc acatagaaaa aattctgcac atagggctca agtattttgt tgttgtttct    2640
ttatcttttc ttgtttttttt gttttttgtt ttttgggggt ttttttgggg tcaagtgcca    2700
ttgaagcatt acctcatgaa aaatatttgt tttgtaataa agataataat tccc          2754
```

AMELIORATION OF CHRONIC KIDNEY DISEASE

CROSS REFERENCE TO RELATED APPLICATIONS

The present invention claims the priority benefit of U.S. Provisional Patent Application 62/250,863, filed Nov. 4, 2015, which is incorporated by reference in its entirety.

STATEMENT REGARDING FEDERAL FUNDING

This invention was made with government support under R01 DK101730 awarded by the National Institutes of Health. The government has certain rights in the invention.

FIELD

Provided herein are compositions and methods for maintenance of normal levels of circulating FGF23, the treatment of chronic kidney disease (CKD) and/or the amelioration or prevention of symptoms, conditions and diseases associated therewith.

BACKGROUND

CKD is a growing public health problem. Beginning early in the course of disease, CKD causes changes in bone and mineral metabolism that contribute to increased risk of fracture, cardiovascular disease and premature mortality. Current therapeutic strategies to improve clinical outcomes in CKD are suboptimal.

SUMMARY

Provided herein are compositions and methods for maintenance of normal levels of circulating FGF23, the treatment of chronic kidney disease (CKD) and/or the amelioration or prevention of symptoms, conditions and diseases associated therewith.

In some embodiments, provided herein are methods comprising administering to a cell, tissue, or subject a composition comprising dentin matrix protein 1 (DMP1) polypeptide, an active fragment or variant thereof, or a nucleic acid encoding DMP1 or an active fragment or variant thereof. In some embodiments, the subject exhibits above normal levels of circulating FGF23. In some embodiments, the subject suffers from chronic kidney disease. In some embodiments, the cell is an osteocyte. In some embodiments, the DMP1 polypeptide comprises a portion with at least 70% (e.g., 70%, 75%, 80%, 85%, 90%, 95%, 100%, or ranges therebetween) sequence identity with SEQ ID NO: 1. In some embodiments, the DMP1 polypeptide comprises a portion with at least 70% (e.g., 70%, 75%, 80%, 85%, 90%, 95%, 100%, or ranges therebetween) sequence identity with SEQ ID NO: 2. In some embodiments, a the DMP1 polypeptide comprises one or more substitutions (e.g., 1, 2, 3, 4, 5, 6, 7, 8, 9, 10, 15, 20, 25, 30, 35, 40, 45, 50, or ranges therebetween) relative to a native DMP1 sequence (e.g., SEQ ID NO: 1 or 2). In some embodiments, the nucleic acid encodes a DMP1 polypeptide comprising a portion with at least 70% (e.g., 70%, 75%, 80%, 85%, 90%, 95%, 100%, or ranges therebetween) sequence identity with SEQ ID NO: 1. In some embodiments, the nucleic acid encodes a DMP1 polypeptide comprising a portion with at least 70% (e.g., 70%, 75%, 80%, 85%, 90%, 95%, 100%, or ranges therebetween) sequence identity with SEQ ID NO: 2. In some embodiments, a the nucleic acid encodes a DMP1 polypeptide with one or more substitutions (e.g., 1, 2, 3, 4, 5, 6, 7, 8, 9, 10, 15, 20, 25, 30, 35, 40, 45, 50, or ranges therebetween) relative to a native DMP1 sequence (e.g., SEQ ID NO: 1 or 2). In some embodiments, the nucleic acid comprises a portion with at least 70% (e.g., 70%, 75%, 80%, 85%, 90%, 95%, 100%, or ranges therebetween) sequence identity with all or a portion of SEQ ID NO: 3.

In some embodiments, provided herein are pharmaceutical compositions comprising a DMP1 polypeptide comprising a portion with at least 70% (e.g., 70%, 75%, 80%, 85%, 90%, 95%, 100%, or ranges therebetween) sequence identity with SEQ ID NO: 1. In some embodiments, provided herein are pharmaceutical compositions comprising a DMP1 polypeptide comprising a portion with at least 70% (e.g., 70%, 75%, 80%, 85%, 90%, 95%, 100%, or ranges therebetween) sequence identity with SEQ ID NO: 2. In some embodiments, a the DMP1 polypeptide comprises one or more substitutions (e.g., 1, 2, 3, 4, 5, 6, 7, 8, 9, 10, 15, 20, 25, 30, 35, 40, 45, 50, or ranges therebetween) relative to a native DMP1 sequence (e.g., SEQ ID NO: 1 or 2). In some embodiments, provided herein are pharmaceutical compositions comprising a nucleic acid encoding a DMP1 polypeptide comprising a portion with at least 70% (e.g., 70%, 75%, 80%, 85%, 90%, 95%, 100%, or ranges therebetween) sequence identity with SEQ ID NO: 1. In some embodiments, provided herein are pharmaceutical compositions comprising a nucleic acid encoding a DMP1 polypeptide comprising a portion with at least 70% (e.g., 70%, 75%, 80%, 85%, 90%, 95%, 100%, or ranges therebetween) sequence identity with SEQ ID NO: 2. In some embodiments, a the nucleic acid encodes a DMP1 polypeptide with one or more substitutions (e.g., 1, 2, 3, 4, 5, 6, 7, 8, 9, 10, 15, 20, 25, 30, 35, 40, 45, 50, or ranges therebetween) relative to a native DMP1 sequence (e.g., SEQ ID NO: 1 or 2). In some embodiments, the nucleic acid comprises a portion with at least 70% (e.g., 70%, 75%, 80%, 85%, 90%, 95%, 100%, or ranges therebetween) sequence identity with all or a portion of SEQ ID NO: 3.

BRIEF DESCRIPTION OF THE DRAWINGS

FIGS. 4A-C. (FIG. 4A) PHEX binds to full length DMP1 and cDMP1. Bone protein extracts from WT and DMP1ko/cDMP1Tg were incubated with anti-PHEX antibody-coated beads. Western Blot shows DMP1 in protein pull-downs. Negative control ((−) CTR) was obtained from uncoated beads to evaluate non-specific binding. (FIG. 4B) Surface Plasmon Resonance (SPR) Sensorgram shows binding and dissociation of soluble human rPHEX to human rDMP1, where DMP1 is attached to the sensor and PHEX is flowed over. The constant of dissociation (KD) between PHEX and the entire DMP1 protein reflecting binding affinity is as strong as the KD obtained previously between rPHEX and the small 19 amino acid MEPE-ASARM peptide. Data are normalized by non-specific binding at baseline and expressed as relative units (RU) of response difference. (FIG. 4C) Dose-dependent binding of rPHEX to rDMP1, represented by quantitation of the SPR sensorgram, confirms binding specificity.

FIGS. 12A-B. DMP1 is a binding partner of PHEX.

DEFINITIONS

Figure 1:
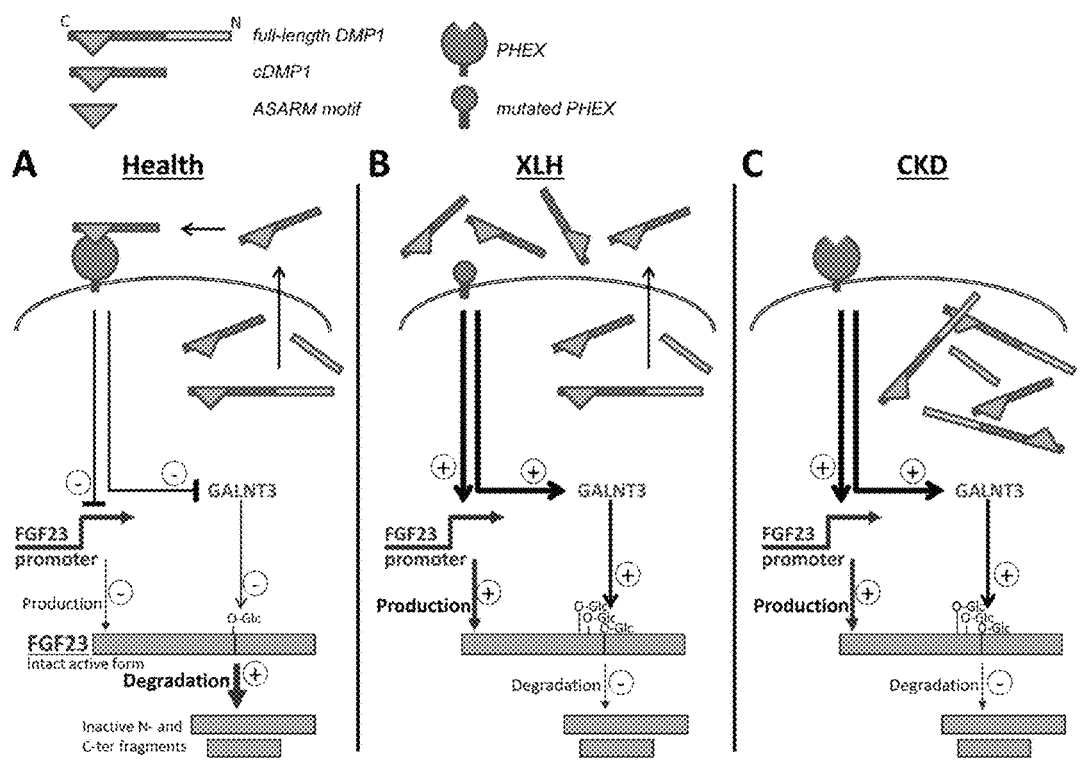
FIG. 1. (Panel A) binding between the bone metalloendopeptidase PHEX and cDMP1 through its ASARM motif maintains basal FGF23 transcription and cleavage in health. (Panel B) In X-Linked Hypophosphatemia (XLH), lack of binding between cDMP1 and mutated PHEX stimulates FGF23 transcription and inhibits FGF23 cleavage, resulting in increased circulating FGF23 levels. (Panel C) In chronic kidney disease (CKD), decreased extracellular DMP1 contributes to increased FGF23 levels through mechanisms that mimic those in XLH.

To facilitate an understanding of the present technology, a number of terms and phrases are defined below. Additional definitions are set forth throughout the detailed description. Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

The terms "protein" and "polypeptide" refer to compounds comprising amino acids joined via peptide bonds and are used interchangeably. A "protein" or "polypeptide" encoded by a gene is not limited to the amino acid sequence encoded by the gene, but includes post-translational modifications of the protein.

Where the term "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein.

The term "portion" when used in reference to a protein (as in "a portion of a given protein") refers to fragments of that protein. The fragments may range in size from four amino acid residues to the entire amino acid sequence minus one amino acid (for example, the range in size includes 4, 5, 6, 7, 8, 9, 10, or 11 . . . amino acids up to the entire amino acid sequence minus one amino acid).

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

As used herein, "modulation" or "to modulate" means either an increase (stimulation) or a decrease (inhibition) in the expression and/or activity of a gene and/or a gene product. For example, expression may be inhibited to potentially prevent tumor proliferation. "Modulation" may also be spatial or temporal modulation, e.g., a change in the time or location where expression or activity occurs.

The terms "oligonucleotide" or "polynucleotide" or "nucleotide" or "nucleic acid" refer to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The terms "an oligonucleotide having a nucleotide sequence encoding a gene" or "a nucleic acid sequence encoding" a specified polypeptide refer to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is frequently that gene which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes; RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

The term "purified" refers to molecules, either nucleic or amino acid sequences, that are removed from their natural environment, isolated or separated. An "isolated nucleic acid sequence" may therefore be a purified nucleic acid sequence. "Substantially purified" molecules are at least 60% free, preferably at least 75% free, and more preferably at least 90% free from other components with which they are naturally associated. As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "composition comprising" a given polynucleotide sequence or polypeptide refers broadly to any composition containing the given polynucleotide sequence or polypeptide. The composition may comprise an aqueous solution. Compositions comprising polynucleotide sequences or fragments thereof may be employed as hybridization probes. In some embodiments, polynucleotide sequences are employed in an aqueous solution containing salts (e.g., NaCl), detergents (e.g., SDS), and other components (e.g., Denhardt's solution, dry milk, salmon sperm DNA, etc.).

As used herein the term "disease" refers to a deviation from the condition regarded as normal or average for members of a species, and which is detrimental to an affected individual under conditions that are not inimical to the majority of individuals of that species (e.g., diarrhea, nausea, fever, pain, inflammation, etc.).

As used herein, the term "administration" refers to the act of giving a drug, prodrug, antibody, or other agent, or therapeutic treatment to a physiological system (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like. "Coadministration" refers to administration of more than one chemical agent or therapeutic treatment (e.g., radiation therapy) to a physiological system (e.g., a subject or in vivo, in vitro, or ex vivo cells, tissues, and organs). As used herein, administration "in combination with" one or more further therapeutic agents includes simultaneous (concurrent) and consecutive administration in any order. "Coadministration" of therapeutic treatments may be concurrent, or in any temporal order or physical combination.

As used herein, the term "treating" includes reducing or alleviating at least one adverse effect or symptom of a disease or disorder through introducing in any way a therapeutic composition of the present technology into or onto the body of a subject. "Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

As used herein, "therapeutically effective dose" refers to an amount of a therapeutic agent sufficient to bring about a beneficial or desired clinical effect. Said dose can be administered in one or more administrations. However, the precise determination of what would be considered an effective dose may be based on factors individual to each patient, including, but not limited to, the patient's age, size, type or extent of disease, stage of the disease, route of administration, the type or extent of supplemental therapy used, ongoing disease process, and type of treatment desired (e.g., aggressive vs. conventional treatment).

As used herein, the term "effective amount" refers to the amount of a composition sufficient to effect beneficial or desired results. An effective amount can be administered in one or more administrations, applications, or dosages and is not intended to be limited to a particular formulation or administration route.

As used herein, the term "pharmaceutical composition" refers to the combination of an active agent with, as desired, a carrier, inert or active, making the composition especially suitable for diagnostic or therapeutic use in vitro, in vivo, or ex vivo.

As used herein, the terms "pharmaceutically acceptable" or "pharmacologically acceptable" refer to compositions that do not substantially produce adverse reactions, e.g., toxic, allergic, or immunological reactions, when administered to a subject.

As used herein, "carriers" include pharmaceutically acceptable carriers, excipients, or stabilizers which are non-toxic to the cell or mammal being exposed thereto at the dosages and concentrations employed. Often the physiologically acceptable carrier is an aqueous pH-buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants.

As used herein, the terms "patient" or "subject" refer to organisms to be treated by the compositions of the present technology or to be subject to various tests provided by the technology. The term "subject" includes animals, preferably mammals, including humans. In a preferred embodiment, the subject is a primate. In an even more preferred embodiment, the subject is a human.

As used herein, the term "sample" is used in its broadest sense. In one sense it can refer to animal cells or tissues. In another sense, it is meant to include a specimen or culture obtained from any source, such as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present technology.

As used herein, the terms "detect", "detecting", or "detection" may describe either the general act of discovering or discerning or the specific observation of a detectably labeled composition.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5 (carboxyhydroxyl-methyl) uracil, 5-fluorouracil, 5 bromouracil, 5-carboxymethylaminomethyl 2 thiouracil, 5 carboxymethyl-aminomethyluracil, dihydrouracil, inosine, N6 isopentenyladenine, 1 methyladenine, 1-methylpseudouracil, 1 methylguanine, 1 methylinosine, 2,2-dimethylguanine, 2 methyladenine, 2 methylguanine, 3-methyl-cytosine, 5 methylcytosine, N6 methyladenine, 7 methylguanine, 5 methylaminomethyluracil, 5-methoxyamino-methyl 2 thiouracil, beta D mannosylqueosine, 5' methoxycarbonylmethyluracil, 5 methoxyuracil, 2 methylthio N6 isopentenyladenine, uracil 5 oxyacetic acid methylester, uracil 5 oxyacetic acid, oxybutoxosine, pseudouracil, queosine, 2 thiocytosine, 5-methyl-2 thiouracil, 2-thiouracil, 4 thiouracil, 5-methyluracil, N-uracil 5 oxyacetic acid methylester, uracil 5 oxyacetic acid, pseudouracil, queosine, 2-thiocytosine, and 2,6 diaminopurine.

DETAILED DESCRIPTION

Provided herein are compositions and methods for maintenance of normal levels of circulating FGF23, the treatment of chronic kidney disease (CKD) and/or the amelioration or prevention of symptoms, conditions and diseases associated therewith. In particular, compositions and methods herein regulate (e.g., inhibit) transcription of FGF23, promote FGF23 cleavage, ameliorate bone and mineral metabolism disorders associated with CKD, prevent the development of cardiac hypertrophy, and/or improve overall patient survival.

CKD is characterized by an early and progressive increase in osteocyte production of fibroblast growth factor (FGF)-23. Elevated FGF23 levels independently predict cardiovascular events, CKD progression, and mortality, indicating for new therapeutic approaches to reduce FGF23 levels in CKD. Dentin matrix protein (DMP)-1 is a bone extracellular matrix protein secreted by osteocytes that inhibits FGF23 and promotes bone formation and mineralization. The cleaved 57 kDa C-terminal fragment of DMP1 (cDMP1) mediates the effects of DMP1. Experiments conducted during development of embodiments herein demonstrate altered osteocyte morphology and reduction in the amount of DMP1 in the bone matrix in CKD mice, which is contemplated to contribute to increased production of FGF23 and its associated negative outcomes. To restore the bone abnormalities observed in CKD towards normal, DMP1 was administered either by injections of recombinant DMP1 protein or by cDMP1 transgene expression in Type IV Collagen alpha-3 subunit (Col4a3)KO CKD mice. Bone growth and architecture improved, elevated circulating FGF23 levels were significantly lowered, and heart structure and function and kidney function improved; survival of the CKD mice was significantly prolonged.

FGF23 is secreted by osteocytes, suppresses calcitriol production and stimulates phosphaturia. FGF23 is a causative factor in several hereditary hypophosphatemic disorders, and additional studies established its critical physiological role in regulating phosphate and vitamin D metabolism in health and in CKD. Increased FGF23 is among the earliest alterations in mineral metabolism in CKD. As CKD progresses, the gradual increase in FGF23 becomes maladaptive, contributing to CKD progression, end-stage renal disease, cardiac dysfunction, and mortality. FGF23 is also implicated in the pathogenesis of left ventricular hypertrophy, which is an important mechanism of congestive heart failure and mortality.

Mechanisms of FGF23 regulation have been poorly understood. Known systemic regulators, such as high levels of parathyroid hormone (PTH), phosphate, calcitriol and calcium, stimulate FGF23 production, but cannot adequately explain increased FGF23 levels in early CKD, because these antedate hyperparathyroidism and hyperphosphatemia, and because CKD is characterized by low levels of calcitriol and calcium rather than high levels. FGF23 excess in hereditary hypophosphatemic disorders supports a critical role for local regulation of FGF23 in bone where the balance between FGF23 transcription and FGF23 cleavage within osteocytes maintains normal circulating FGF23 levels.

Inactivating mutations of phosphate-regulating gene with homology to endopeptidase on the X chromosome (PHEX) causes X-Linked Hypophosphatemia (XLH—homologous Hyp mouse).

Inactivating mutations of dentin matrix protein (DMP)-1 cause Autosomal Recessive Hypophosphatemic Rickets (ARHR—homologous DMP1ko mouse). Although PHEX and DMP1 mutations induce overlapping hypophosphatemic rickets phenotypes with marked elevations of circulating intact FGF23 levels, the molecular mechanisms of FGF23 regulation by PHEX and DMP1 have been mostly unknown.

DMP1 is a 106 kDa extracellular matrix protein expressed in osteocytes and a member of the SIBLINGs protein family. The full-length latent DMP1 protein is cleaved into 37 kDa N-terminal and 57 kDa C-terminal (cDMP1) peptide fragments. SIBLINGs all share a characteristic RGD motif for integrin binding and an acidic serine aspartate-rich motif (ASARM). In DMP1, both motifs are located on the highly phosphorylated cDMP1 peptide.

PHEX is a 105 kDa cell membrane metalloendopeptidase that is also expressed in osteocytes, but no definitive substrate has yet been defined. PHEX has a high binding affinity for the ASARM sequence, and peptides containing the ASARM motif accumulate in Hyp bone matrix as a consequence of PHEX-inactivation. Although PHEX binds in vitro to two other SIBLINGs proteins (matrix extracellular phosphoglycoprotein [MEPE], osteopontin) through their ASARM sequences, DMP1 is the only SIBLING for which an inactivating mutation fully recapitulates the PHEX-mutant phenotype.

Cleavage of biologically active intact FGF23 (iFGF23) occurs at a conserved RXXR recognition motif and generates inactive N- and C-terminal fragments. Poorly defined subtilisin-like proprotein convertases cleave FGF23, and GalNAc transferase 3 (GALNT3) protects newly synthesized FGF23 from cleavage by O-glycosylation of the cleavage site. Mutations of GALNT3 or its FGF23 glycosylation sites cause Hyperphosphatemic Familial Tumoral Calcinosis due to low iFGF23 levels and resultant hyperphosphatemia. These mutations demonstrate that O-glycosylation is critical for secretion of biologically active iFGF23.

In physiological conditions, circulating FGF23 levels are tightly regulated by a balance between Fgf23 transcription and FGF23 cleavage within osteocytes, which are the main source of FGF23. In cases of pathological excess of FGF23, such as XLH, ARHR or CKD, circulating FGF23 levels rise due to both increased transcription and decreased cleavage of FGF23. Experiments conducted during development of embodiments herein indicate that cDMP1 deficiency unbalances FGF23 transcription and FGF23 cleavage, and that cDMP1 overexpression normalizes FGF23 cleavage and transcription in DMP1ko mice, but not in Hyp mice, providing evidence that PHEX is required for cDMP1 to regulate FGF23.

CKD is characterized by increased FGF23 production and decreased FGF23 cleavage, but previous studies have not systematically evaluated the effects of DMP1 in CKD. Increased total DMP1 mRNA and protein expression is observed in bone from patients and animals with CKD. Experiments conducted during development of embodiments herein demonstrate reduced cDMP1 in the bone ECM of the Col4a3ko mouse model of CKD compared to WT mice, indicating that secretion of cDMP1 is impaired in CKD despite increased total DMP1 expression.

Experiments conducted during development of embodiments herein demonstrate DMP1 acts to inhibit FGF23 transcription and promote FGDF23 cleavage, and that increasing DMP1 levels restores normal circulating FGF23 levels, treats CKD, and/or ameliorate bone and mineral metabolism disorders associated therewith.

In some embodiments, compositions and methods are provided for increasing the level and/or expression of DMP1 or variants/fragment thereof (e.g., lacking the N-terminus, a C-terminal polypeptide, etc.) or fragments thereof for reducing FGF23 levels and/or the treatment of CKD and/or bone and mineral metabolism disorders associated therewith. In some embodiments, DMP1 polypeptides or variants/fragments thereof (e.g., lacking the N-terminus, a C-terminal polypeptide) are administered. In other embodiments, nucleic acids encoding P1 polypeptides or variants/fragments thereof (e.g., a C-terminal polypeptide, lacking the N-terminus) are administered (e.g., gene therapy).

In some embodiments, a nucleic acid is used to modulate the level of DMP1. Accordingly, some embodiments of the technology described herein relate to the use of gene editing or genome editing to modulate the expression and/or activity of FGF23, DMP1, and/or PHEX. For example, some embodiments comprise increasing the activity and/or expression of DMP1. Some embodiments comprise use of gene editing or genome editing to overexpress DMP1.

In some embodiments, provided herein is the administration of nucleic acids encoding polypeptides (e.g. DMP1 polypeptides or variants/fragments thereof (e.g., a C-terminal polypeptide, lacking the N-terminus) which inhibit FGF23 expression (e.g., transcription) and/or activity (e.g., promote FGF23 cleavage). In some embodiments, nucleic acids encoding DMP1 polypeptides or variants/fragments thereof are administered (e.g. to a subject, cell or cells (e.g., osteocyte cells)) as an inhibitor of FGF23. In some embodiments, nucleic acids encoding a fragment (e.g., peptide, polypeptide) of a DMP1 (e.g., comprising the C-terminal portion) are administered. In some embodiments, a nucleic acid encoding a polypeptide with at least 50% homology to WT DMP1 (SEQ ID NO:1) is administered (e.g. at least 60% homology, at least 70% homology, at least 80% homology, at least 90% homology, at least 95% homology, at least 99% homology, etc.). In some embodiments, a nucleic acid encoding a polypeptide with at least 50% homology to cDMP1 (SEQ ID NO:2) is administered (e.g. at least 60% homology, at least 70% homology, at least 80% homology, at least 90% homology, at least 95% homology, at least 99% homology, etc.).

In some embodiments, provided herein is the delivery of exogenous nucleic acids encoding DMP1 polypeptides or variants/fragments thereof (e.g., lacking the N-terminus), or the delivery of DMP1 polypeptides themselves (e.g., recombinant DMP1, synthetic DMP1, etc.) to a subject via any suitable method. In preferred embodiments, nucleic acids are delivered within suitable vectors. The present invention is not limited to any particular vector. Indeed, a variety of vectors may be used to deliver the nucleic acids.

In some embodiments, the technology provided herein relates to gene therapy. For example, some embodiments use genetic manipulation to modulate the expression of biomarkers such as those described herein (e.g., FGF23, DMP1, and/or PHEX) or biomarkers associated therewith. Examples of genetic manipulation include, but are not limited to, gene knockout (such as by removing the genetic rearrangement from the chromosome using, e.g., by recombination), gene knock-down, expression of antisense constructs with or without inducible promoters, and the like, overexpression, etc. Delivery of nucleic acid construct to cells in vitro or in vivo may be conducted using any suitable method. A suitable method is one that introduces the nucleic acid construct into the cell such that the desired event occurs (e.g., expression of an antisense construct). Genetic therapy may also be used to deliver siRNA or other interfering molecules that are expressed in vivo (e.g., upon stimulation by an inducible promoter).

Introduction of molecules carrying genetic information into cells is achieved by any of various methods including, but not limited to, directed injection of naked DNA constructs, bombardment with gold particles loaded with said constructs, and macromolecule-mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors and their use in gene transfer are well known (e.g., see PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety). Such vectors and methods have been shown to provide very efficient in vivo gene transfer into a variety of solid tumors in animal models and into human solid tumor xenografts in immune-deficient mice.

Vectors may be administered to subject in a variety of well-known ways, e.g., administered into tumors or tissue associated with tumors by using direct injection or administration via the blood or lymphatic circulation (See e.g., PCT publication 99/02685 herein incorporated by reference in its entirety). Exemplary dose levels of adenoviral vector are preferably 108 to 1011 vector particles added to the perfusate.

In certain embodiments, the nucleic acids are delivered via an adenovirus vector. (See e.g., Westfall et al., Meth. Cell Biol. 32:307-322 (1998); and U.S. Pat. Nos. 6,451,596, 6,083,750, 6,063,622, 6,057,158, or 5,994,132, all of which are herein incorporated by reference). In some embodiments, a nucleic acid encoding a DMP1 polypeptide or fragment thereof is delivered via an adeno-associated vector (AAV). In some embodiments, the AAV vector integrates into the genome of the cells to which it is administered (e.g., a patient's cells (e.g., endothelial cells)). A number of AAV vectors which have been developed for gene therapy are useful in the present invention (See e.g., U.S. Pat. Nos. 5,173,414; 5,139,941; and 5,843,742; PCT publications WO92/01070 and WO93/03769; Lebkowski et al., Mol. Cell. Biol. 8:3988-3996 (1988); Carter, Curr. Opin. Biotech. 3:533-39, (1992); Muzyczka, Curr. Top, Microbiol. Immunol. 158:97-129, (1994); Kotin, Human Gene Ther. 5:793-801, (1994); Shelling and Smith, Gene Ther. 1:165-69, (1994); Zhou et al., J. Exp. Med. 179:1867-1875, (1994); U.S. Pat. Nos. 6,451,596, 6,083,750, 6,063,622, 6,057,158, or 5,994,132; Ferrari et al., Nature Med. 3(11):1295-97, (1997); and Gregorevic et al., Nature. Med. 10(8): 828 (2004), each of which is incorporated herein by reference in its entirety). In certain embodiments, a DMP1 protein or fragment thereof is incorporated into an AAV2 vector in which expression is driven by a vascular endothelial-cadherin promoter (Investigative Ophthalmology & Visual Science, February 2012, Vol. 53, No. 2; pp. 574-585; herein incorporated by reference in its entirety).

In some embodiments, recombinant adenovirus vectors are constructed by homologous recombination of a shuttle vector containing a nucleic acid encoding a DMP1 protein and the full-length adenovirus DNA following co-transfection into a cell line. In some embodiments, the full-length adenovirus DNA is provided from pJM17 which is a 0-100 map unit (m.u.) derivative of adenovirus serotype (Ad5) that contains a partial deletion in the E3 region and a 4.3-kb pBRX insert at 3.7 m.u. (See e.g., Graham and Prevec, Manipulation of Adenovirus Vectors, in Gene Transfer and Expression Protocols, E. J. Murray ed., Humana, Clifton, N.J. (1991); and Becker et al., Use of Recombinant Adenovirus for Metabolic Engineering of Mammalian Cells, in Methods in Cell Biology, Vol 43 M. G. Roth ed., Academic Press, N.Y. (1994); Grahm and Prevec, Methods Mol. Biol. 7, 109 (1991); herein incorporated by reference in their entireties). In some embodiments, a shuttle vector comprises 0-1 m.u. and 9-16 m.u. of the Ad5 genome flanking an expression cassette containing the nucleic acid encoding a DMP1 protein. The present invention is not limited by the type of AAV or the methods of construction thereof.

In other embodiments, the nucleic acid encoding a DMP1 polypeptide or fragment thereof is delivered via a liposome or naked DNA plasmid. In some embodiments, the liposome is a cationic liposome (See e.g., U.S. Pat. Nos. 5,908,777 and 5,676,954 each incorporated herein by reference in their entireties; Hug and Sleight, Biochim. Biophys. Acta. 1097: 1-17, (1991); Straubinger et al., in Methods of Enzymology, Vol. 101 pp. 512-527 (1993); Felgner et al., Nature 337: 387-388, (1989); and Felgner et al., PNAS (1987) 84:7413-7416) (1987); herein incorporated by reference in their entireties). An example of a commercially available cationic liposome carrier useful in the present invention is LIPO-FECTIN (Bethesda Research Laboratories Life Technologies, Inc., Gaithersburg Md.).

In some embodiments, a vector comprising nucleic acid encoding a DMP1 polypeptide or a fragment thereof further includes a suitable promoter (e.g., cell specific promoter) and/or enhancer, and also any necessary ribosome binding sites, polyadenylation site, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In some embodiments, a DNA sequence in the expression vector is operatively linked to an appropriate expression control sequence(s) (e.g., promoter) to direct mRNA synthesis. Promoters useful in embodiments herein include, but are not limited to, the LTR or SV40 promoter, the *E. coli*. lac or trp, the phage lambda $P_L$ and $P_R$, T3 and T7 promoters, HSV thymidine kinase, and mouse metallothionein-I promoters and other promoters known to control expression of genes in eukaryotic cells (e.g., osteocyte cells) or their viruses. In some embodiments, recombinant expression vectors include selectable markers permitting transformation of the host cell. In some embodiments, the promoter is a tissue specific and/or inducible promoter.

In some embodiments, transcription of the DNA encoding peptides and/or polypeptides described herein by higher eukaryotes is increased by inserting an enhancer sequence into the vector. Enhancers are cis-acting elements of DNA, usually about from 10 to 300 bp that act on a promoter to increase its transcription; Enhancers useful in the present invention include, but are not limited to, the SV40 enhancer (e.g., 100 to 270 base pairs on the late side of the replication origin), a cytomegalovirus early promoter enhancer, the polyoma enhancer (e.g., on the late side of the replication origin), and adenovirus enhancers.

In other embodiments, the expression vector also contains a ribosome binding site for translation initiation and a transcription terminator. In still other embodiments of the present invention, the vector includes appropriate sequences for amplifying expression.

In some embodiments, the technology comprises use of gene editing or genome editing. Gene editing, or genome editing, is a type of genetic engineering in which DNA is inserted, replaced, or removed from a genome using nucleases. The nucleases may be artificially engineered. Alternately, the nucleases may be found in nature. The nucleases create specific double-stranded breaks (DSBs) at desired locations in the genome. The cell's endogenous repair mechanisms subsequently repairs the induced break(s) by natural processes, such as homologous recombination (HR) and non-homologous end-joining (NHEJ). Nucleases include, for example, Zinc Finger Nucleases (ZFNs), Transcription Activator-Like Effector Nucleases (TALENs), CRISPR, (e.g., the CRISPR/Cas system), and engineered meganuclease re-engineered homing endonucleases. CRISPR nucleases include for example a Cas nuclease, a Cpf1 nuclease, a C2c1 nuclease, a C2c3 nuclease, and a C2c3 nuclease. In some embodiments, gene editing or genome editing comprises use of CRISPR.

In some embodiments, the nuclease comprises a CRISPR/Cas system. The CRISPR (clustered regularly interspaced short palindromic repeats) locus, which encodes RNA components of the system, and the Cas (CRISPR-associated) locus, which encodes proteins (Jansen et al., 2002. Mol. Microbiol. 43: 1565-1575; Makarova et al., 2002. Nucleic Acids Res. 30: 482-496; Makarova et al., 2006. Biol. Direct 1: 7; Haft et al., 2005. PLoS Comput. Biol. 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand breaks in four sequential steps. First, two non-coding RNAs, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called "adaptation", (ii) expression of the relevant proteins, as well as expression and processing of the array, followed by (iii) RNA-mediated interference with the alien nucleic acid. Thus, in the bacterial cell, several of the so-called "Cas" proteins are involved with the natural function of the CRISPR/Cas system and serve roles in functions such as insertion of the alien DNA.

In some embodiments, provided herein is the administration of polypeptides (e.g. DMP1 or fragments thereof) which inhibit FGF23 expression and/or decrease levels of circulating active FGF23 (e.g., by promoting cleavage of FGF23) and/or treat or prevent CKD and related bone conditions. In some embodiments, DMP1 or a fragment thereof is administered (e.g. to a subject, cell or cells (e.g., osteocyte cells)) as an inhibitor of FGF23. In some embodiments, a fragment (e.g., peptide, polypeptide) of a DMP1 (e.g., comprising the C-terminal portion) is administered. In some embodiments, a polypeptide with at least 50% homology to DMP1 (SEQ ID NO:1) is administered (e.g. at least 60% homology, at least 70% homology, at least 80% homology, at least 90% homology, at least 95% homology, at least 99% homology, etc.). In some embodiments, a polypeptide with at least 50% homology to a portion of DMP1 (SEQ ID NO:1) is administered (e.g. at least 60% homology, at least 70% homology, at least 80% homology, at least 90% homology, at least 95% homology, at least 99% homology, etc.). In some embodiments, a polypeptide with at least 50% homology to cDMP1 (SEQ ID NO:2) is administered (e.g. at least 60% homology, at least 70% homology, at least 80% homology, at least 90% homology, at least 95% homology, at least 99% homology, etc.).

In some embodiments, polypeptides herein are isolated and/or purified (or substantially isolated and/or substantially purified). Accordingly, the invention provides polypeptide in substantially isolated form. In some embodiments, polypeptides are isolated from other polypeptides as a result of solid phase protein synthesis, for example. Alternatively, polypeptides can be substantially isolated from other proteins after cell lysis from recombinant production. Standard methods of protein purification (e.g., HPLC) can be employed to substantially purify polypeptides.

In some embodiments, the present invention provides a preparation of polypeptides in a number of formulations, depending on the desired use. For example, where the polypeptide is substantially isolated (or even nearly completely isolated from other proteins), it can be formulated in a suitable medium solution for storage (e.g., under refrigerated conditions or under frozen conditions). Such preparations may contain protective agents, such as buffers, preservatives, cryprotectants (e.g., sugars such as trehalose), etc. The form of such preparations can be solutions, gels, etc., and the inventive polypeptide can, in some embodiments, be prepared in lyophilized form. Moreover, such preparations can include other desired agents, such as small molecules or even other polypeptides and proteins, if desired. Indeed, the invention provides such a preparation comprising a mixture of different embodiments of the inventive polypeptide (e.g., a plurality of polypeptide species as described herein).

In some embodiments, the present invention also provides a pharmaceutical composition comprising of one or more polypeptides (e.g., DMP1) or nucleic acids (e.g., vector) encoding DMP1, and a pharmaceutically acceptable carrier. Any carrier which can supply a polypeptide and/or nucleic acid without destroying the vector within the carrier is a suitable carrier, and such carriers are well known in the art.

In some embodiments, provided herein are DMP1 polypeptides that retain the activity (e.g., binding FGF23 promoter, inhibiting FGF23 expression, promoting cleavage of FGF23, etc.) of WT DMP1. In some embodiments, a DMP1 polypeptide is at least 50% sequence identical (e.g., 50% . . . 60% . . . 70% . . . 75% . . . 80% . . . 85% . . . 90% . . . 95% . . . 98% . . . 99%) to DMP! (SEQ ID NO:1) or cDMP1 (SEQ ID NO: 2).

In some embodiments, DMP1 polypeptides comprise substitutions relative to WT DMP1. Examples of these variants are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of DMP1, or fragments thereof, containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., Biochemistry, pg. 17-21, 2nd ed, WH Freeman and Co., 1981). Whether a change in the amino acid sequence of a peptide results in a functional polypeptide can be readily determined by assessing the ability of the variant peptide to function in a fashion similar to full length SEQ ID NO: 2. Peptides having more than one replacement can readily be tested in the same manner.

In some embodiments, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (including, but not limited to, FADE (Mitchell et al., (2004). Molec. Simul. 30, 97-106); MAPS (Ban et al., Proceedings of the 8th Annual International Conference on Research in Computational Molecular Biology, 2004, 205-212), SYBYL (Tripos, Inc, St. Louis, Mo.); and PyMOL (available on the Internet web site of sourceforge)).

In some embodiments, methods comprise comparing a biomarker (e.g., DMP1, PHEX, FGF23) level to a reference value/range or a threshold. In some embodiments, deviation of the biomarker(s) level from the reference value/range, or exceeding or failing to meet the threshold, is indicative of a diagnosis, prognosis, etc. for the subject.

In any of the embodiments described herein, each biomarker may be a protein biomarker. In any of the embodiments described herein, the method may comprise contacting biomarkers of the sample from the subject with a set of biomarker capture reagents, wherein each biomarker capture reagent of the set of biomarker capture reagents specifically binds to a biomarker being detected. In some embodiments, each biomarker capture reagent of the set of biomarker capture reagents specifically binds to a different biomarker being detected. In any of the embodiments described herein, each biomarker capture reagent may be an antibody or an aptamer. In some embodiments, the antibody that is used for diagnostic and/or prognostic technologies is the same or similar to an antibody described herein for use as a therapeutic (or a fragment, derivative, or modification of such an antibody).

In some embodiments, a biomarker is an RNA transcript. In any of the embodiments described herein, the method may comprise contacting biomarkers of the sample from the subject with a set of biomarker capture reagents, wherein each biomarker capture reagent of the set of biomarker capture reagents specifically binds to a biomarker being detected. In some embodiments, each biomarker capture reagent of the set of biomarker capture reagents specifically binds to a different biomarker being detected. In any of the embodiments described herein, each biomarker capture reagent may be a nucleic acid probe.

In any of the embodiments described herein, methods further comprise treating the subject for increased FGF23 levels, CDK, or conditions/symptoms resulting therefrom. In some embodiments, biomarkers described herein are monitored before, during, and/or after treatment.

In some embodiments, a biomarker detection/quantification assay is performed along with one or more additional assays, for example, in order to evaluate CDK in a subject (e.g., to provide a prognosis). In some embodiments, a biomarker panel comprises 2, 3, 4, 5, 6, 7, 8, 9, 10, 11, 12, 13, 14, 15, 16, 17, 18, 19, 20 . . . 30 . . . 40, or more biomarkers. In some embodiments, a biomarker panel comprises fewer than 100 biomarkers (e.g., <100, <90, <80, <70, <60, <50, <40, <30, <20, <10, <5). In some embodiments, the number and identity of biomarkers in a panel are selected based on the sensitivity and specificity for the particular combination of biomarker values.

In some embodiments, methods comprise contacting a sample or a portion of a sample from a subject with at least one detection/capture reagent, wherein each capture reagent specifically binds a biomarker (e.g., protein, nucleic acid, etc.) whose presence and/or level is being detected. In some embodiments, capture reagents are antibodies, aptamers, probes, etc. In some embodiments, a method comprises detecting the level of a first biomarker (or panel of biomarkers) by contacting a sample with detection and/or capture reagents specific for that biomarker and then detection one or more additional biomarkers.

The presence of a biomarker or a biomarker level for the biomarkers described herein can be detected using any of a variety of analytical methods. In one embodiment, a biomarker level is detected using a capture reagent. In various embodiments, the capture reagent is exposed to the biomarker in solution or is exposed to the biomarker while the capture reagent is immobilized on a solid support. In other embodiments, the capture reagent contains a feature that is reactive with a secondary feature on a solid support. In these embodiments, the capture reagent is exposed to the biomarker in solution, and then the feature on the capture reagent is used in conjunction with the secondary feature on the solid support to immobilize the biomarker on the solid support. The capture reagent is selected based on the type of analysis to be conducted. Capture reagents include but are not limited to aptamers, antibodies, adnectins, ankyrins, other antibody mimetics and other protein scaffolds, autoantibodies, chimeras, small molecules, F(ab')2 fragments, single chain antibody fragments, Fv fragments, single chain Fv fragments, nucleic acids, lectins, ligand-binding receptors, affybodies, nanobodies, imprinted polymers, avimers, peptidomimetics, hormone receptors, cytokine receptors, and synthetic receptors, and modifications and fragments of these.

In some embodiments, biomarker presence or level is detected using a biomarker/capture reagent complex. In some embodiments, the biomarker presence or level is derived from the biomarker/capture reagent complex and is detected indirectly, such as, for example, as a result of a reaction that is subsequent to the biomarker/capture reagent interaction, but is dependent on the formation of the biomarker/capture reagent complex.

In some embodiments, biomarker presence or level is detected directly from the biomarker in a biological sample.

In some embodiments, biomarkers are detected using a multiplexed format that allows for the simultaneous detection of two or more biomarkers in a biological sample. In some embodiments of the multiplexed format, capture reagents are immobilized, directly or indirectly, covalently or non-covalently, in discrete locations on a solid support. In some embodiments, a multiplexed format uses discrete solid supports where each solid support has a unique capture reagent associated with that solid support, such as, for example quantum dots. In some embodiments, an individual device is used for the detection of each one of multiple biomarkers to be detected in a biological sample. Individual devices are configured to permit each biomarker in the biological sample to be processed simultaneously. For example, a microtiter plate can be used such that each well in the plate is used to analyze one or more of multiple biomarkers to be detected in a biological sample.

In one or more of the foregoing embodiments, a fluorescent tag is used to label a component of the biomarker/capture reagent complex to enable the detection of the biomarker level. In various embodiments, the fluorescent label is conjugated to a capture reagent specific to any of the biomarkers described herein using known techniques, and the fluorescent label is then used to detect the corresponding biomarker level. Suitable fluorescent labels include rare earth chelates, fluorescein and its derivatives, rhodamine and its derivatives, dansyl, allophycocyanin, PBXL-3, Qdot 605, Lissamine, phycoerythrin, Texas Red, and other such compounds.

In some embodiments, the detection method includes an enzyme/substrate combination that generates a detectable signal that corresponds to the biomarker level (e.g., using the techniques of ELISA, Western blotting, isoelectric focusing). Generally, the enzyme catalyzes a chemical alteration of the chromogenic substrate which can be measured using various techniques, including spectrophotometry, fluorescence, and chemiluminescence. Suitable enzymes include, for example, luciferases, luciferin, malate dehydrogenase, urease, horseradish peroxidase (HRPO), alkaline phosphatase, beta-galactosidase, glucoamylase, lysozyme, glucose oxidase, galactose oxidase, and glucose-6-phosphate dehydrogenase, uricase, xanthine oxidase, lactoperoxidase, microperoxidase, and the like.

In some embodiments, the biomarker levels for the biomarkers described herein is detected using any analytical methods including, singleplex aptamer assays, multiplexed aptamer assays, singleplex or multiplexed immunoassays, mRNA expression profiling, miRNA expression profiling, mass spectrometric analysis, histological/cytological methods, etc. as discussed below.

Immunoassay methods are based on the reaction of an antibody to its corresponding target or analyte and can detect the analyte in a sample depending on the specific assay format. To improve specificity and sensitivity of an assay method based on immuno-reactivity, monoclonal antibodies and fragments thereof are often used because of their specific epitope recognition. Polyclonal antibodies have also been successfully used in various immunoassays because of their increased affinity for the target as compared to monoclonal antibodies. Immunoassays have been designed for use with a wide range of biological sample matrices. Immunoassay formats have been designed to provide qualitative, semi-quantitative, and quantitative results.

Quantitative results are generated through the use of a standard curve created with known concentrations of the specific analyte to be detected. The response or signal from an unknown sample is plotted onto the standard curve, and a quantity or level corresponding to the target in the unknown sample is established.

Numerous immunoassay formats have been designed. ELISA or EIA can be quantitative for the detection of an analyte. This method relies on attachment of a label to either the analyte or the antibody and the label component includes, either directly or indirectly, an enzyme. ELISA tests may be formatted for direct, indirect, competitive, or sandwich detection of the analyte. Other methods rely on labels such as, for example, radioisotopes ($I^{125}$) or fluorescence. Additional techniques include, for example, agglutination, nephelometry, turbidimetry, Western blot, immunoprecipitation, immunocytochemistry, immunohistochemistry, flow cytometry, Luminex assay, and others (see ImmunoAssay: A Practical Guide, edited by Brian Law, published by Taylor & Francis, Ltd., 2005 edition; herein incorporated by reference in its entirety).

Exemplary assay formats include enzyme-linked immunosorbent assay (ELISA), radioimmunoassay, fluorescent, chemiluminescence, and fluorescence resonance energy transfer (FRET) or time resolved-FRET (TR-FRET) immunoassays. Examples of procedures for detecting biomarkers include biomarker immunoprecipitation followed by quantitative methods that allow size and peptide level discrimination, such as gel electrophoresis, capillary electrophoresis, planar electrochromatography, and the like.

Any of the methods for detection can be performed in any format that allows for any suitable preparation, processing, and analysis of the reactions. This can be, for example, in multi-well assay plates (e.g., 96 wells or 384 wells) or using any suitable array or microarray. Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting a detectable label.

Measuring mRNA in a biological sample may, in some embodiments, be used as a surrogate for detection of the level of a corresponding protein in the biological sample. Thus, in some embodiments, a biomarker or biomarker panel described herein can be detected by detecting the appropriate RNA.

In some embodiments, mRNA expression levels are measured, e.g., to assess expression of FGF23, PHEX, DMP1, etc. In some embodiments, mRNA expression (e.g., transcript absolute quantity and/or transcript relative quantity, e.g., relative to a reference and/or a control) is measured by reverse transcription quantitative polymerase chain reaction (RT-PCR followed with qPCR). RT-PCR is used to create a cDNA from the mRNA. The cDNA may be used in a qPCR assay to produce fluorescence as the DNA amplification process progresses. By comparison to a standard curve, qPCR can produce an absolute measurement such as number of copies of mRNA per cell. Embodiments provide that mRNA levels are quantified for isoforms and differently spliced forms of the RNA transcripts.

In additional embodiments, northern blots, microarrays, RNAseq, Invader assays, and/or RT-PCR combined with capillary electrophoresis is/are used to measure expression levels of mRNA in a sample. See Gene Expression Profiling: Methods and Protocols, Richard A. Shimkets, editor, Humana Press, 2004; herein incorporated by reference in its entirety.

In some embodiments, a biomarker described herein may be used in molecular imaging tests. For example, an imaging agent can be coupled to a capture reagent, which can be used to detect the biomarker in vivo.

In vivo imaging technologies provide non-invasive methods for determining the state of a particular disease in the body of an individual. For example, entire portions of the body, or even the entire body, may be viewed as a three dimensional image, thereby providing valuable information concerning morphology and structures in the body. Such technologies may be combined with the detection of the biomarkers described herein to provide information concerning the biomarker in vivo.

Advances in the use of in vivo molecular imaging technologies include the development of new contrast agents or labels, such as radiolabels and/or fluorescent labels, which can provide strong signals within the body; and the development of powerful new imaging technology, which can detect and analyze these signals from outside the body, with sufficient sensitivity and accuracy to provide useful information. The contrast agent can be visualized in an appropriate imaging system, thereby providing an image of the portion or portions of the body in which the contrast agent is located. The contrast agent may be bound to or associated with a capture reagent, with a peptide or protein, or an oligonucleotide (for example, for the detection of gene expression), or a complex containing any of these with one or more macromolecules and/or other particulate forms.

In some embodiments, the biomarkers described herein (e.g., FGF23, PHEX, etc.) may be detected in a variety of tissue samples using histological or cytological methods. In some embodiments, one or more capture reagent/s specific to the corresponding biomarker/s are used in a cytological evaluation of a sample and may include one or more of the following: collecting a cell sample, fixing the cell sample, dehydrating, clearing, immobilizing the cell sample on a microscope slide, permeabilizing the cell sample, treating for analyte retrieval, staining, destaining, washing, blocking, and reacting with one or more capture reagent/s in a buffered solution. In another embodiment, the cell sample is produced from a cell block.

In some embodiments, one or more capture reagent/s specific to the corresponding biomarkers are used in a histological evaluation of a tissue sample and may include one or more of the following: collecting a tissue specimen, fixing the tissue sample, dehydrating, clearing, immobilizing the tissue sample on a microscope slide, permeabilizing the tissue sample, treating for analyte retrieval, staining, destaining, washing, blocking, rehydrating, and reacting with capture reagent/s in a buffered solution. In another embodiment, fixing and dehydrating are replaced with freezing.

In some embodiments, a biomarker "signature" for a given diagnostic or prognostic test contains one or more biomarkers (e.g., a set of markers), each marker having characteristic levels in the populations of interest. Characteristic levels, in some embodiments, may refer to the mean or average of the biomarker levels for the individuals in a particular group. In some embodiments, a diagnostic/prognostic method described herein can be used to assign an unknown sample from an individual into one of two or more groups: high risk, lower risk, treatment-responsive, treatment-unresponsive, healthy, etc. The assignment of a sample into one of two or more groups is known as classification, and the procedure used to accomplish this assignment is known as a classifier or a classification method. Classification methods may also be referred to as scoring methods.

There are many classification methods that can be used to construct a diagnostic classifier from a set of biomarker levels. In some instances, classification methods are performed using supervised learning techniques in which a data set is collected using samples obtained from individuals within two (or more, for multiple classification states) distinct groups one wishes to distinguish. Since the class (group or population) to which each sample belongs is known in advance for each sample, the classification method can be trained to give the desired classification response. It is also possible to use unsupervised learning techniques to produce a diagnostic classifier.

In some embodiments, the results are analyzed and/or reported (e.g., to a patient, clinician, researcher, investigator, etc.). Results, analyses, and/or data (e.g., signature, disease score, diagnosis, recommended course, etc.) are identified and/or reported as an outcome/result of an analysis. A result may be produced by receiving or generating data (e.g., test results) and transforming the data to provide an outcome or result. An outcome or result may be determinative of an action to be taken. In some embodiments, results determined by methods described herein can be independently verified by further or repeat testing.

In some embodiments, analysis results are reported (e.g., to a health care professional (e.g., laboratory technician or manager; physician, nurse, or assistant, etc.), patient, researcher, investigator, etc.). In some embodiments, a result is provided on a peripheral, device, or component of an apparatus. For example, sometimes an outcome is provided by a printer or display. In some embodiments, an outcome is reported in the form of a report. Generally, an outcome can be displayed in a suitable format that facilitates downstream use of the reported information.

Generating and reporting results from the methods described herein comprises transformation of biological data (e.g., presence or level of biomarkers) into a representation of the characteristics of a subject (e.g., likelihood of mortality, likelihood corresponding to treatment, etc.). Such a representation reflects information not determinable in the absence of the method steps described herein. Converting biologic data into understandable characteristics of a subject allows actions to be taken in response such information.

In some embodiments, a downstream individual (e.g., clinician, patient, etc.), upon receiving or reviewing a report comprising one or more results determined from the analyses provided herein, will take specific steps or actions in response. For example, a decision about whether or not to treat the subject, and/or how to treat the subject is made.

The term "receiving a report" as used herein refers to obtaining, by a communication means, a written and/or graphical representation comprising results or outcomes of analysis. The report may be generated by a computer or by human data entry, and can be communicated using electronic means (e.g., over the internet, via computer, via fax, from one network location to another location at the same or different physical sites), or by another method of sending or receiving data (e.g., mail service, courier service and the like). In some embodiments the outcome is transmitted in a suitable medium, including, without limitation, in verbal, document, or file form. The file may be, for example, but not limited to, an auditory file, a computer readable file, a paper file, a laboratory file or a medical record file. A report may be encrypted to prevent unauthorized viewing.

As noted above, in some embodiments, systems and method described herein transform data from one form into another form (e.g., from biomarker levels to diagnostic/prognostic determination, etc.). In some embodiments, the terms "transformed", "transformation", and grammatical derivations or equivalents thereof, refer to an alteration of data from a physical starting material (e.g., biological sample, etc.) into a digital representation of the physical starting material (e.g., biomarker levels), a condensation/representation of that starting material (e.g., risk level), or a recommended action (e.g., treatment, no treatment, etc.).

Any combination of the biomarkers described herein (e.g., FGF23, PHEX, DMP1, etc.) can be detected using a suitable kit, such as for use in performing the methods disclosed herein. The biomarkers described herein may be combined in any suitable combination, or may be combined with other markers not described herein. Furthermore, any kit can contain one or more detectable labels as described herein, such as a fluorescent moiety, etc.

In some embodiments, a kit includes (a) one or more capture reagents for detecting one or more biomarkers in a biological sample, and optionally (b) one or more software or computer program products for providing a diagnosis/prognosis for the individual from whom the biological sample was obtained. Alternatively, rather than one or more computer program products, one or more instructions for manually performing the above steps by a human can be provided.

In some embodiments, a kit comprises a solid support, a capture reagent, and a signal generating material. The kit can also include instructions for using the devices and reagents, handling the sample, and analyzing the data. Further the kit may be used with a computer system or software to analyze and report the result of the analysis of the biological sample.

The kits can also contain one or more reagents (e.g., solubilization buffers, detergents, washes, or buffers) for processing a biological sample. Any of the kits described herein can also include, e.g., buffers, blocking agents, mass spectrometry matrix materials, serum/plasma separators, antibody capture agents, positive control samples, negative control samples, software and information such as protocols, guidance and reference data.

In some embodiments, following analysis of biomarkers (e.g., DMP1, PHEX, FGF23, etc.) using the methods/reagents/kits herein, the subject is appropriately treated (e.g., to increase DMP1 levels, to decrease FGF23 levels, etc.).

Methods of treatment comprise, e.g., methods that inhibit the activity of FGF23 (e.g., via cleavage), methods that decrease FGF23 expression, methods that increase DMP1 and/or PHEX levels, etc. For example, in some embodiments the technology provides a method for inhibiting expression (e.g., transcription) of FGF23. In some embodiments, inhibiting expression (e.g., transcription) of FGF23 finds use to treat or study diseases involving aberrant FGF23 activity.

EXPERIMENTAL

Experiments were conducted during development of embodiments herein to compare mechanisms of FGF23 regulation by PHEX and DMP1 in osteocytes in PHEX and DMP1 mutant mice. It was considered how PHEX and DMP1 mutations could lead to the Hyp and Dmp1$^{ko}$ phenotypes: 1) distinct pathways, 2) distinct pathways regulating a common intermediary unknown factor, or 3) common pathways with DMP1 downstream or upstream of PHEX directly regulating FGF23. While the first two possibilities imply additive function, the 3$^{rd}$ indicates that either the single or double mutation would cause identical phenotypes. Thus, a compound mutant mouse model was created and compared WT, Hyp, Dmp1$^{ko}$, and Hyp/Dmp1$^{ko}$ mice. It was found that compound mutant mice had the same gross appearance as single mutants, and demonstrated non-additive effects on activation of the FGF23 promoter in mature osteocytes versus single mutant Hyp or Dmp1ko mice. This resulted in similar levels of FGF23, phosphate and calcitriol, and an identical bone phenotype in single versus compound mutant mice. These data indicate that PHEX and DMP1 regulate FGF23 via a common pathway.

Figure 2:
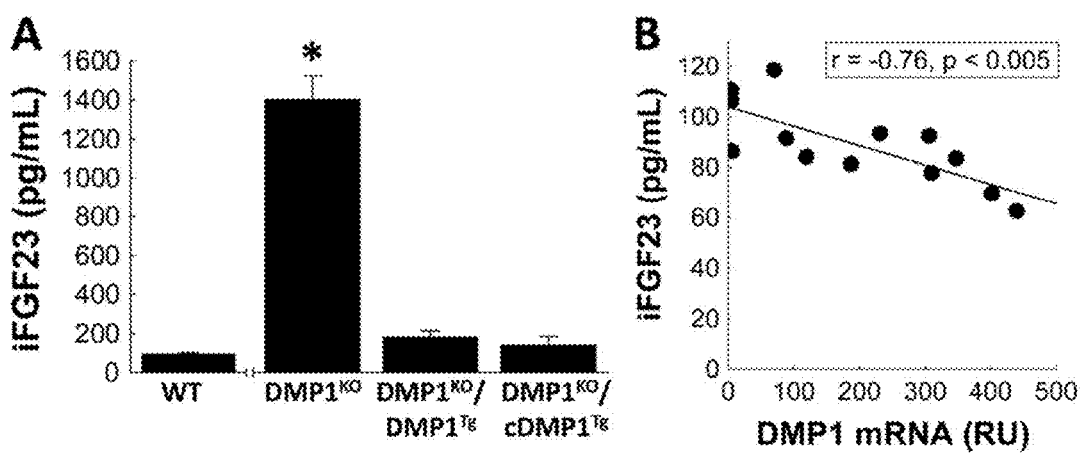
FIG. 2. (Panel A) Serum iFGF23 levels of WT, DMP1KO, DMP1KO/DMP1Tg and DMP1KO/cDMP1Tg mice. Values are mean±SE from 5 week-old mice (n=8). (*) p<0.05 vs. WT. (Panel B) Pearson correlation of serum iFGF23 levels and bone mRNA expression of DMP1, in WT, DMP1Tg and cDMP1Tg mice.

Experiments were conducted during development of embodiments of the present invention that showed that overexpression of full length DMP1 rescues the phenotype of Dmp1ko mice in which PHEX functions normally. Additionally, overexpression of cDMP1 was sufficient to induce the same effect, suggesting that cDMP1 is the functional fragment of DMP1 and that the N-terminal fragment of DMP1 is not involved in FGF23 regulation. Indeed, high circulating levels of FGF23 in Dmp1ko mice were restored to normal in Dmp1ko/cDMP1Tg mice (FIG. 2A).

Figure 3:
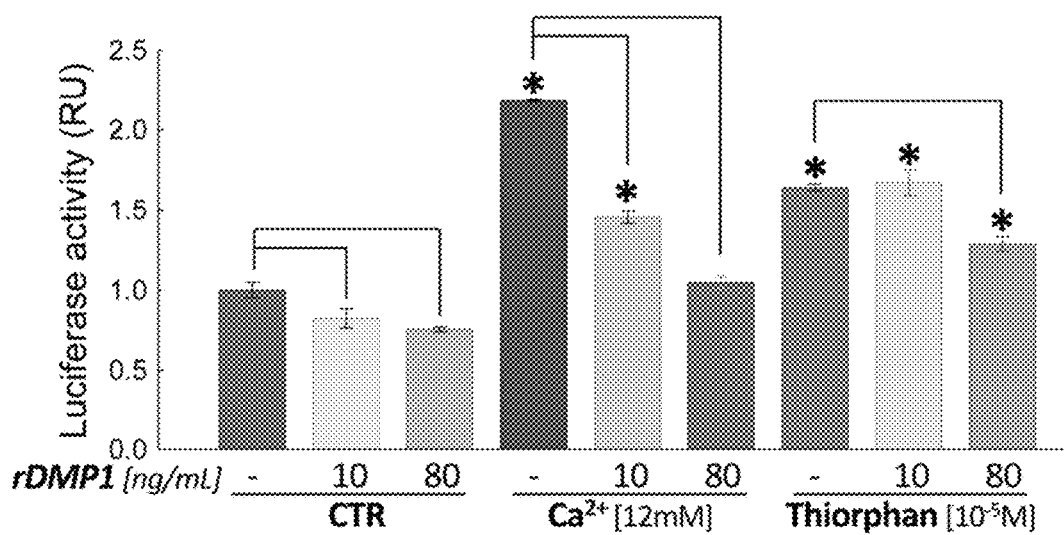
FIG. 3. PHEX-dependent effects of mouse rDMP1 on FGF23 promoter activity. MC3T3-E1 cells were transfected with a 1.3 Kb luciferase reporter FGF23 promoter and cultured for 10 days. Fully differentiated cells were treated for the last 12 h of culture for detection of acute promoter activation by Luciferase assay. Ca2+ and Thiorphan were used as positive control for promoter activation and PHEX-inhibitor, respectively.

Experiments conducted during development of embodiments of the present invention tested the effects of mouse recombinant DMP1 (rDMP1) on FGF23 promoter activity in MC3T3-E1 osteoblast/osteocyte cell line (FIG. 3). DMP1 inhibited FGF23 promoter activity in a dose-dependent manner in control cells or in association with Ca2+-induction of FGF23 promoter. Consistent with increased FGF23 promoter activity observed in vivo in PHEX-mutant Hyp osteocytes, inhibition of PHEX activity by metalloprotease inhibitor thiorphan, stimulated FGF23 promoter activity in MC3T3-E1 cultures. The dose-dependent inhibition of FGF23 promoter activity by rDMP1 was blocked in presence of thiorphan. These data indicate that the transcriptional regulation of FGF23 by DMP1 is dependent on PHEX function.

To test the effects of cDMP1 in the presence or absence of PHEX function, cDMP1 was overexpressed in WT and Hyp mice. Despite significant increases in levels of calcitriol, which are known to stimulate FGF23, FGF23 levels were normal in cDMP1Tg mice (Table 1), indicating that cDMP1 exerts a direct inhibitory role on FGF23 production. This is further confirmed by the negative correlation between bone DMP1 mRNA expression and circulating FGF23 levels in mice with normal PHEX function (FIG. 2B). In PHEX-mutant Hyp/cDMP1Tg mice, cDMP1 overexpression did not rescue elevated bone expression of FGF23 as it did in Dmp1ko/cDMP1Tg mice. These contrasting results indicate that cDMP1 requires PHEX to downregulate FGF23 mRNA expression.

TABLE 1

Serum biochemistries of WT and cDMP1$^{Tg}$ mice

|  | WT | cDMP1$^{Tg}$ |
|---|---|---|
| FGF23 (pg/mL) | 94.1 ± 8.1 | 88.2 ± 11.1 |
| 1,25(OH)$_2$D (pM) | 168.6 ± 19.2 | 236.1 ± 18.0* |
| PTH (pg/mL) | 44.6 ± 7.9 | 28.9 ± 5.0* |
| Pi (mg/dl) | 8.2 ± 0.4 | 9.0 ± 0.3 |
| Ca$^{2+}$ (mg/dL) | 7.8 ± 0.3 | 7.8 ± 0.2 |

Values are mean ± SE from 5 week-old mice (n = 8).
*p < 0.05 vs. WT

Both PHEX and DMP1 are expressed by osteocytes. The ASARM sequence binds to PHEX. Co-immunoprecipitation (coIP) of PHEX and DMP1 were performed in endogenous bone protein extracts to test the presence of binding between PHEX and cDMP1. Magnetic beads were covalently coated with a PHEX antibody (Ab) and incubated with protein extracts isolated from WT or DMP1ko/cDMP1Tg mice.

Figure 4C:
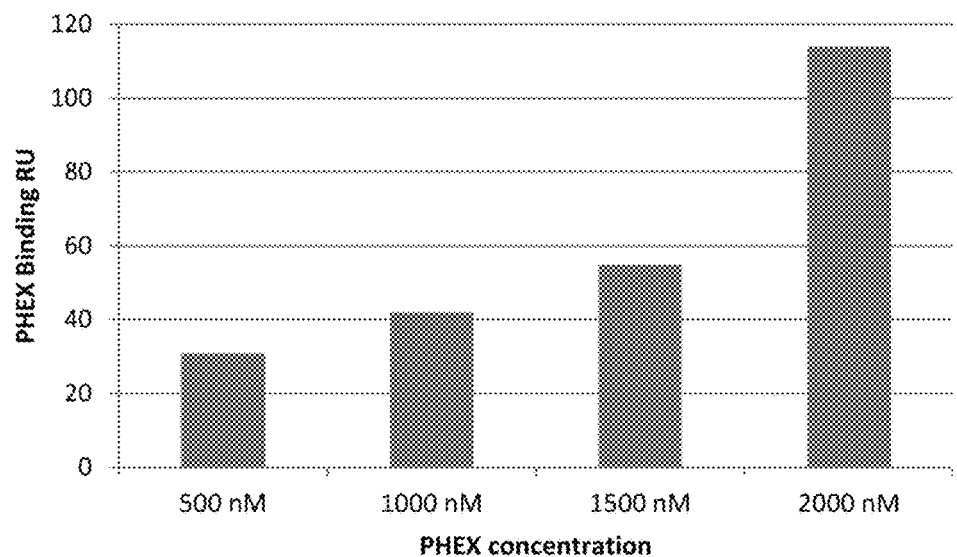

Detection of DMP1 in the protein pull-downs eluted from the beads was performed by Western Blot analysis using an Ab targeting the C-terminus region (FIG. 4A). In the WT, results show presence of two proteins corresponding to full-length DMP1 (~100 kDa) and cDMP1 (~55 kDa). In the DMP1ko/cDMP1Tg extracts in which full-length DMP1 is not expressed, only cDMP1 fragments were detected. Human recombinant PHEX and DMP1 proteins were used to study binding between PHEX and DMP1 by Surface Plasmon Resonance. Results demonstrate that calculated affinity of PHEX binding to DMP1 protein is as strong as its affinity for the much smaller 19 amino acids ASARM peptide (FIG. 4B-C). These data indicate specific binding between PHEX and both full length DMP1 and cDMP1. The N-terminal DMP1 fragment was did not detected by coIP, indicating that PHEX binds to DMP1 through a cDMP1 motif.

Figure 5:
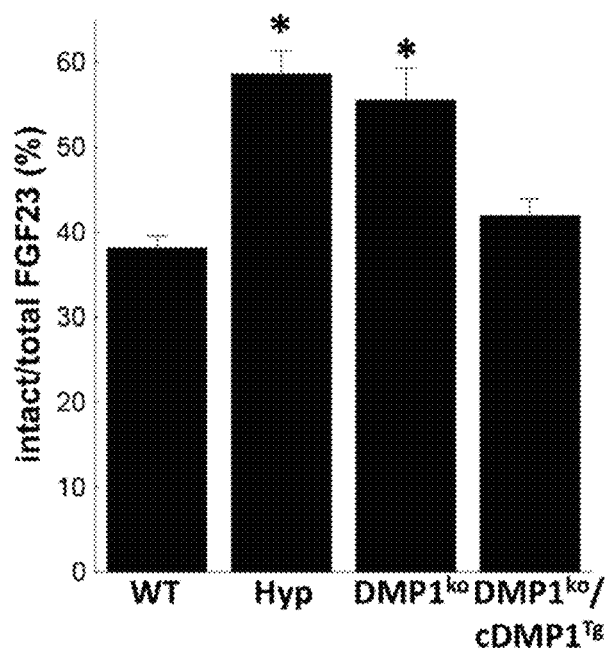
FIG. 5. Proportion of intact/total FGF23 in the circulation of 5 week-old WT, Hyp, DMP1ko and DMP1ko/cDMP1Tg mice. Data are mean±SE (n=8). (*) p<0.05 vs. WT.

Circulating levels of biologically active FGF23 are determined by the balance between FGF23 transcription and FGF23 cleavage within osteocytes, which can be indirectly assessed by simultaneously measuring FGF23 with two different commercially available assays. The C-terminal FGF23 assay (cFGF23—Immutopics) captures both intact FGF23 and its cleaved C-terminal fragments, whereas the intact assay (iFGF23—Kainos) exclusively detects intact hormone. The ratio of iFGF23:cFGF23 values yields insight into the relative proportion of FGF23 species in circulation that are intact and thus, the balance between FGF23 production and cleavage. In Hyp and Dmp1ko mice, it was found that the ratio of iFGF23:cFGF23 was increased by ~20% (FIG. 5), suggesting relatively less FGF23 cleavage compared to WT mice. In contrast, overexpression of cDMP1 in DMP1ko mice prevented the increase in intact/total FGF23 (FIG. 5), indicating that cDMP1 stimulates FGF23 cleavage. Since these effects were not observed in Hyp mice, the interaction of cDMP1 with PHEX appears to be critical to regulation of FGF23 cleavage. In Hyp/cDMP1Tg mice, the proportion of iFGF23 was further increased compared to Hyp mice, indicating an opposite PHEX-independent effect of cDMP1 on FGF23 degradation. In aggregate, these data indicate the PHEX/cDMP1 axis plays an important role in regulating FGF23 cleavage, and that the stimulation of FGF23 cleavage by cDMP1 is PHEX-dependent.

Figure 6:
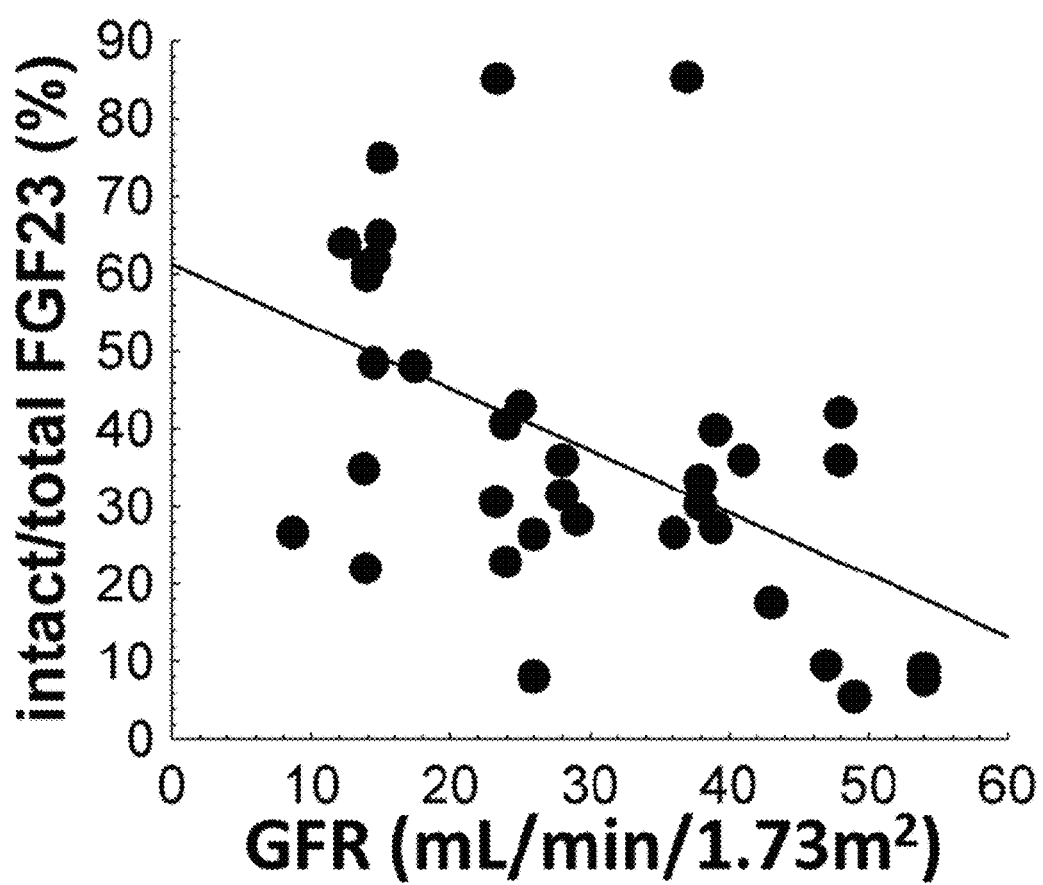
FIG. 6. As GFR declines, proportion of iFGF23 rises. Negative correlation between intact/total FGF23 and GFR among CKD patients, n=35, r=−0.51, p<0.005.
Figure 7:
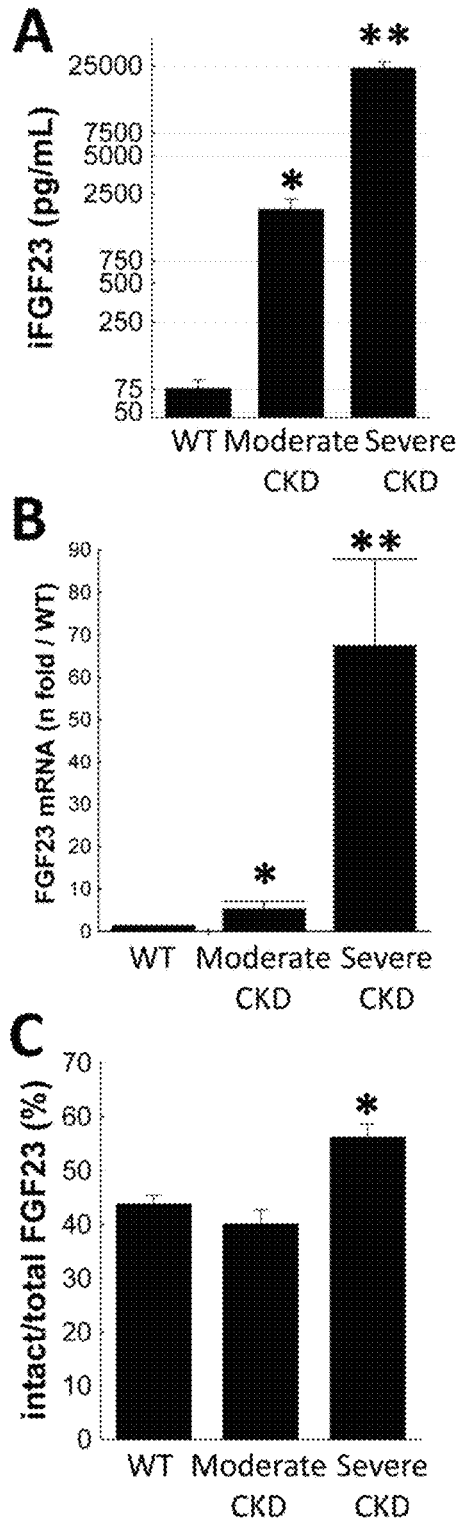
FIG. 7. (Panel A) Serum iFGF23 (log scale), (Panel B) FGF23 mRNA expression in bone and (Panel C) intact/total FGF23 levels in WT and Col4a3ko mice, (n>5), p<0.05 (*) vs. WT, (**) vs. moderate CKD.
Figure 8:
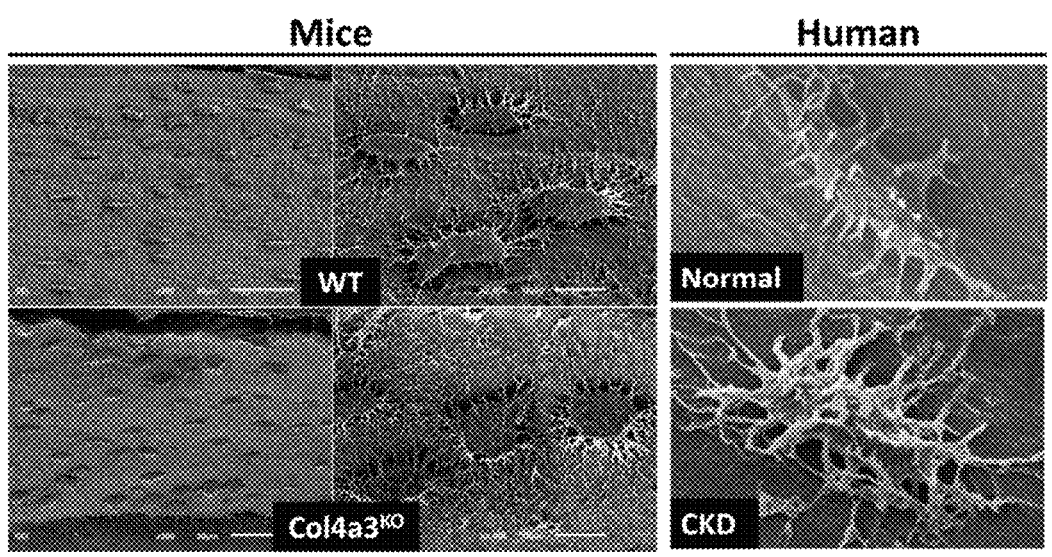
FIG. 8. Mouse and human osteocyte morphology by SEM acid-etching.

Results indicates an impact of CKD on cDMP1 and regulation of FGF23 CKD in the form of increased transcription and decreased cleavage of FGF23 from altered osteocytes in humans and mice. As glomerular filtration rate (GFR) declines, circulating iFGF23 concentrations increase. Experiments conducted during development of embodiments herein show that as FGF23 levels rise in CKD, the ratio of intact/total FGF23 correlated negatively with GFR in 35 CKD patients (FIG. 6). These data indicate that reduced FGF23 cleavage contributes to increased iFGF23 in CKD. The collagen 4 alpha 3 knockout (Col4a3ko) Alport mouse is a validated model of progressive CKD that displays many characteristics of human CKD, including early increases in FGF23 (FIG. 7A). Osteocytes are the main source of circulating FGF23 in Col4a3ko mice, and that bone FGF23 mRNA expression increases by ~70-fold compared to WT controls (FIG. 7B). Additionally, Col4a3ko mice with severe CKD display higher proportions of intact/total FGF23 (FIG. 7C), suggesting that increased transcription and decreased cleavage of iFGF23 contribute to elevated iFGF23 levels, similar to human CKD. Renal FGF23 clearance is not altered in Col4a3ko mice, since injected, cleavage-resistant rFGF23 (R179Q) has a similar serum half-life in WT and Col4a3ko mice. Altered osteocyte organization and morphology in Col4a3ko mice (fewer osteocytes than controls, disordered cell bodies switched from spindle to round shape) that are strikingly similar to the osteocyte morphology observed in human CKD (FIG. 8). Taken together, these data indicate morphologic and functional alterations of the osteocyte in CKD, and that altered regulation of both FGF23 transcription and cleavage contribute to increased FGF23 levels in CKD.

Figure 9:
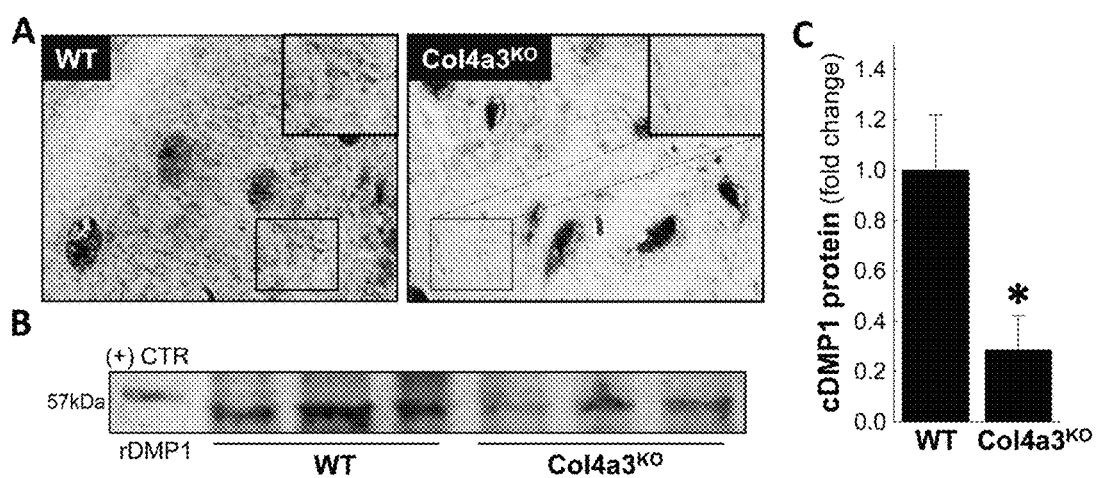
FIG. 9. Reduced cDMP1 in bone extracellular matrix (ECM) of 8 week-old CKD mice. (Panel A) Immunohistochemistry staining of DMP1 (Vector-SG black) in cortical bone osteocytes from WT and Col4a3ko mice (×20). Identical exposure time was used for image acquisition. Squares indicate comparable areas showing lighter ECM DMP1 staining in Col4a3ko than in WT. (Panel B) Western Blot detection of cDMP1 in decellularized bone matrices isolated from WT and Col4a3ko mice and (Panel C) Quantification of WB shown in (Panel B) indicating a 3-fold reduction of cDMP1 in ECM from Col4a3ko mice.

To understand whether osseous alteration of the PHEX/DMP1 axis increases FGF23 production in CKD, mRNA expression of PHEX and DMP1 was measured by RT-PCR analysis in bones of WT and Col4a3ko mice. Expression of PHEX was progressively reduced 4-fold whereas DMP1 expression increased 1.5-fold in Col4a3ko compared to WT mice (Table 2). Increased DMP1 mRNA expression was consistent with previous findings in patients with CKD. cDMP1 immunostaining and Western Blot demonstrate that the amount of matrix extracellular cDMP1 is −3-fold lower in Col4a3ko than in WT mice (FIG. 9), indicating a defect in DMP1 processing in Col4a3ko bones. It is contemplated that this defect is either be due to deficient DMP1 cleavage into N- and C-terminal fragments or decreased cDMP1 secretion from osteocytes into the extracellular matrix. It is contemplated that increased DMP1 expression is a compensatory mechanism in response to increased FGF23 expression, and that the lack of extracellular matrix cDMP1 contributes to continuously increased FGF23 production in CKD.

TABLE 2

Bone mRNA expression in Col4a3$^{ko}$ mice

| | Moderate CKD | Severe CKD |
|---|---|---|
| DMP1 | +1.5* | +1.2 |
| PHEX | −2.0* | −4.1* |

Values are n-fold compared to WT (n < 5).
*$p < 0.05$ vs. WT.

Figure 10:
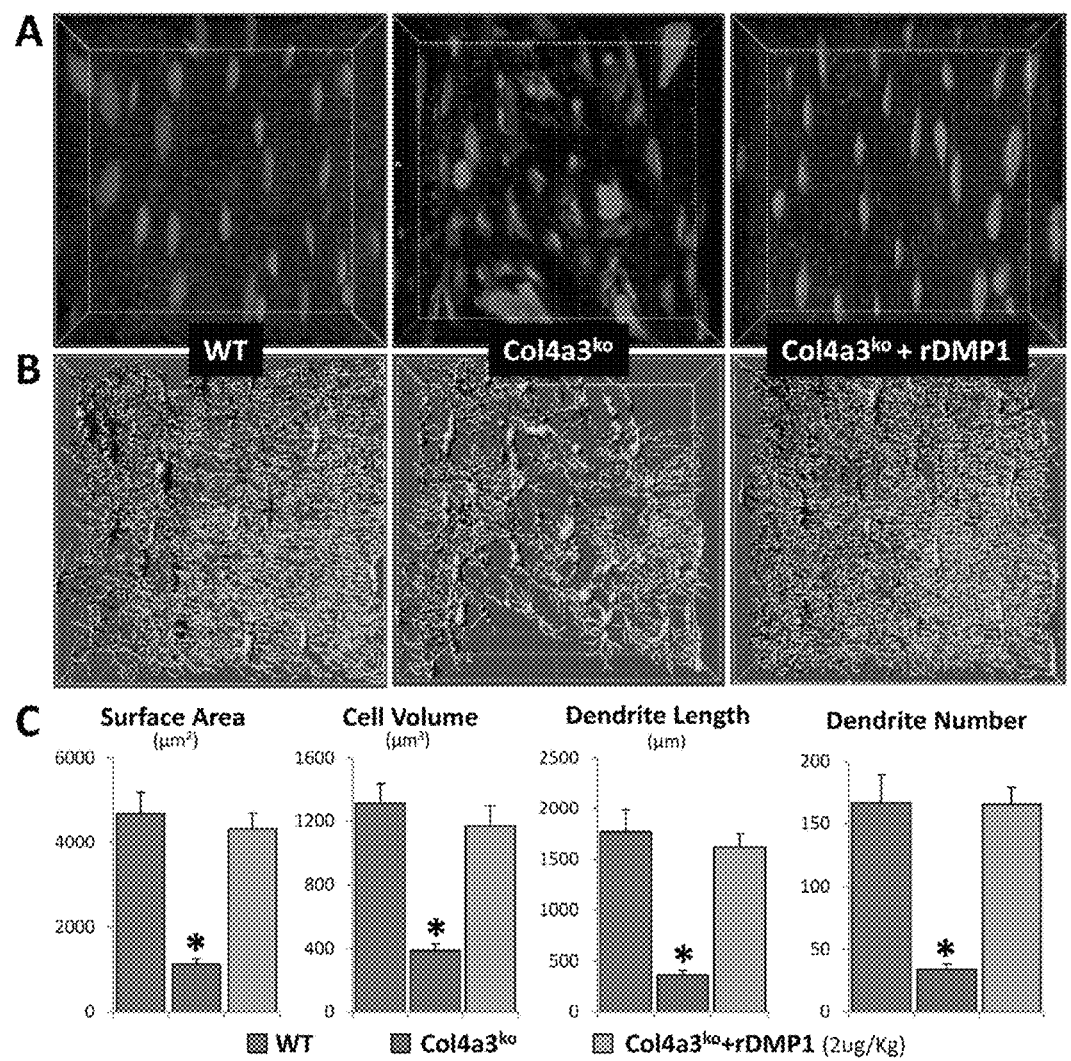
FIG. 10. DMP1 administration rescues osteocyte alterations in CKD. (Panel A) Whole bone FITC staining. Osteocyte body is rounder is Col4a3ko than in WT and reverts to a spindle shape in DMP1-treated Col4a3ko mice. (Panel B) Imaris modelisation of FITC stained osteocyte network. (Panel C) Quantification of panel B. Data were obtained in collaboration with Dr. Feng on 8 week-old WT and Col4a3ko (severe CKD) mice injected daily with 2 ug/Kg of mouse rDMP1 or NaCl for 7 days. Data are mean±SE (n=15-20 osteocytes). (*) p<0.05 vs. WT.
Figure 11:
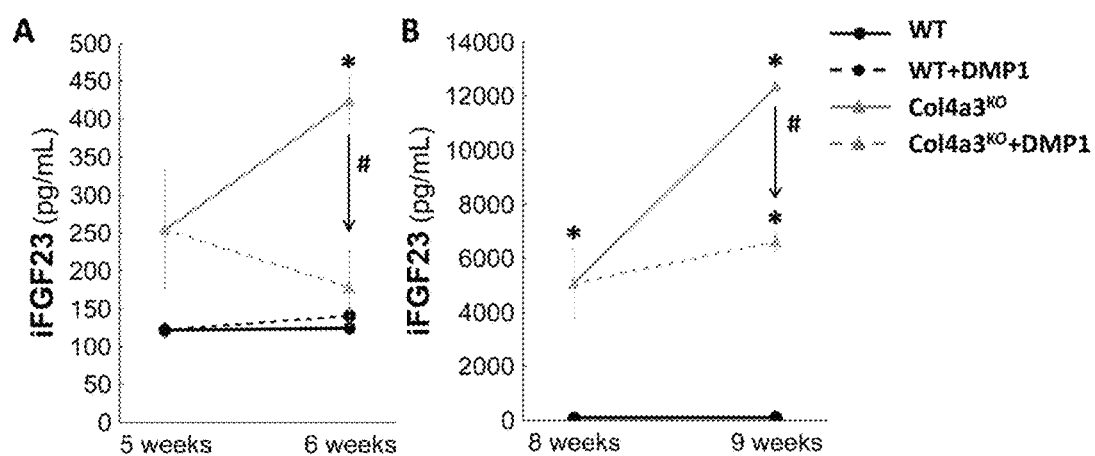
FIG. 11. Correction of iFGF23 levels in CKD by DMP1 administration. (Panel A) Five week-old Col4a3ko (moderate CKD), (Panel B) 8 week-old (severe CKD) Col4a3ko and age-matched WT littermates were injected daily with 2 ug/Kg of mouse rDMP1 for 7 days. Data are mean±SE (n=3). p<0.05 (*) vs. WT and (#) vs. Col4a3ko+DMP1.
Figure 12B:
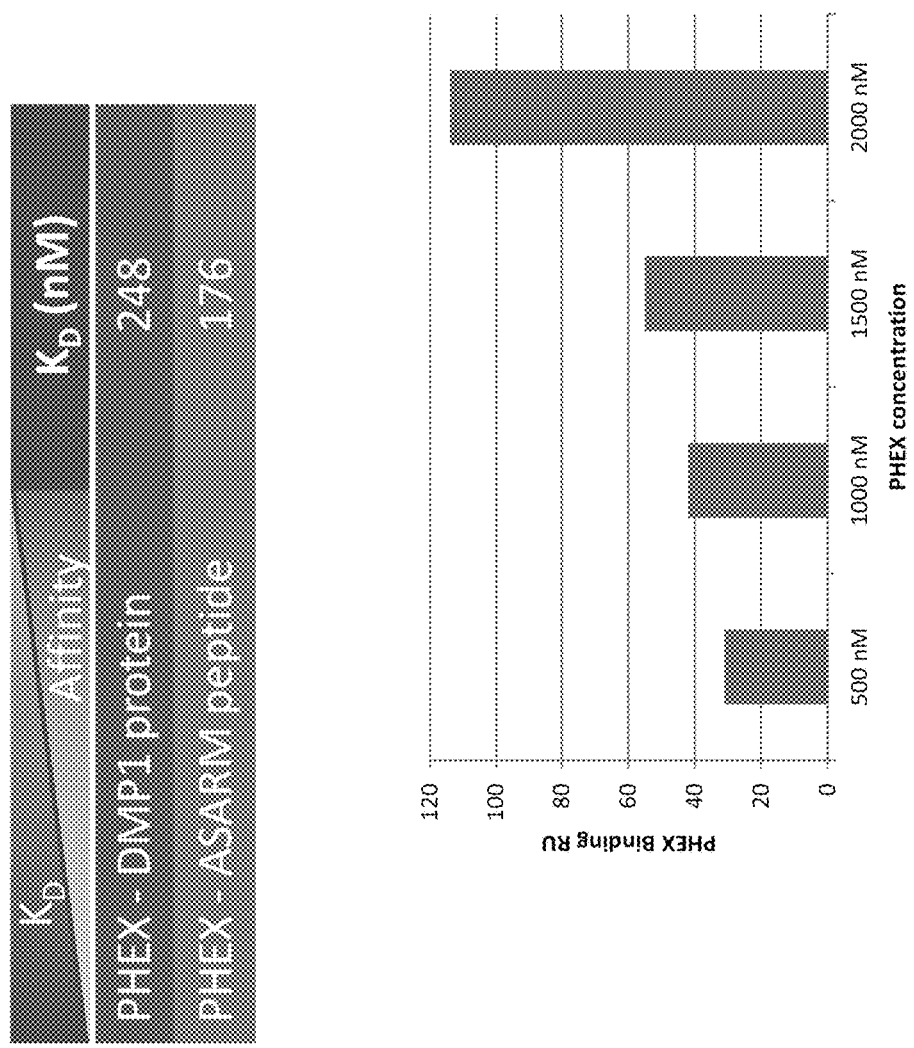
Figure 13:
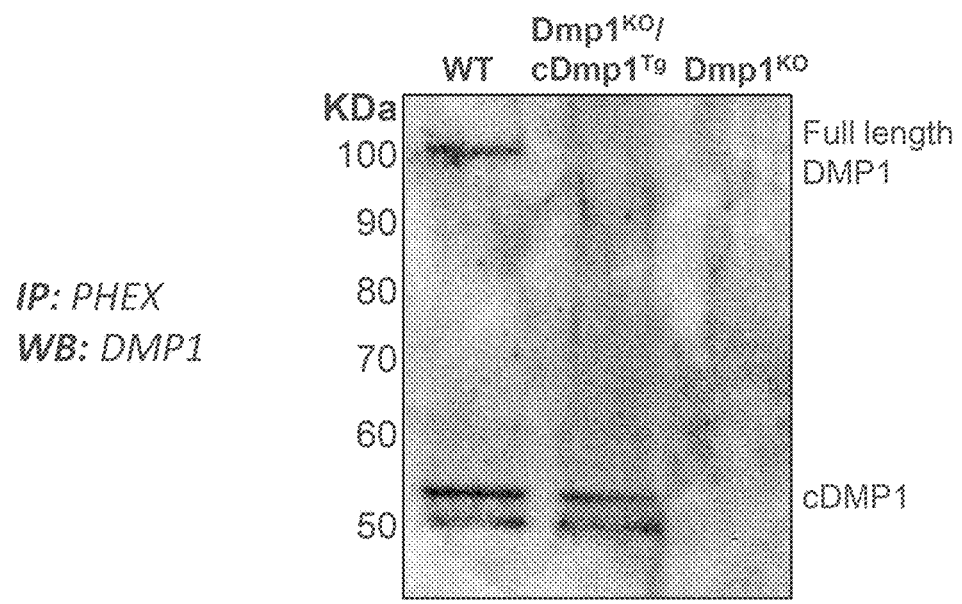
FIG. 13. PHEX binds to DMP1 through a C-terminal region.
Figure 14:
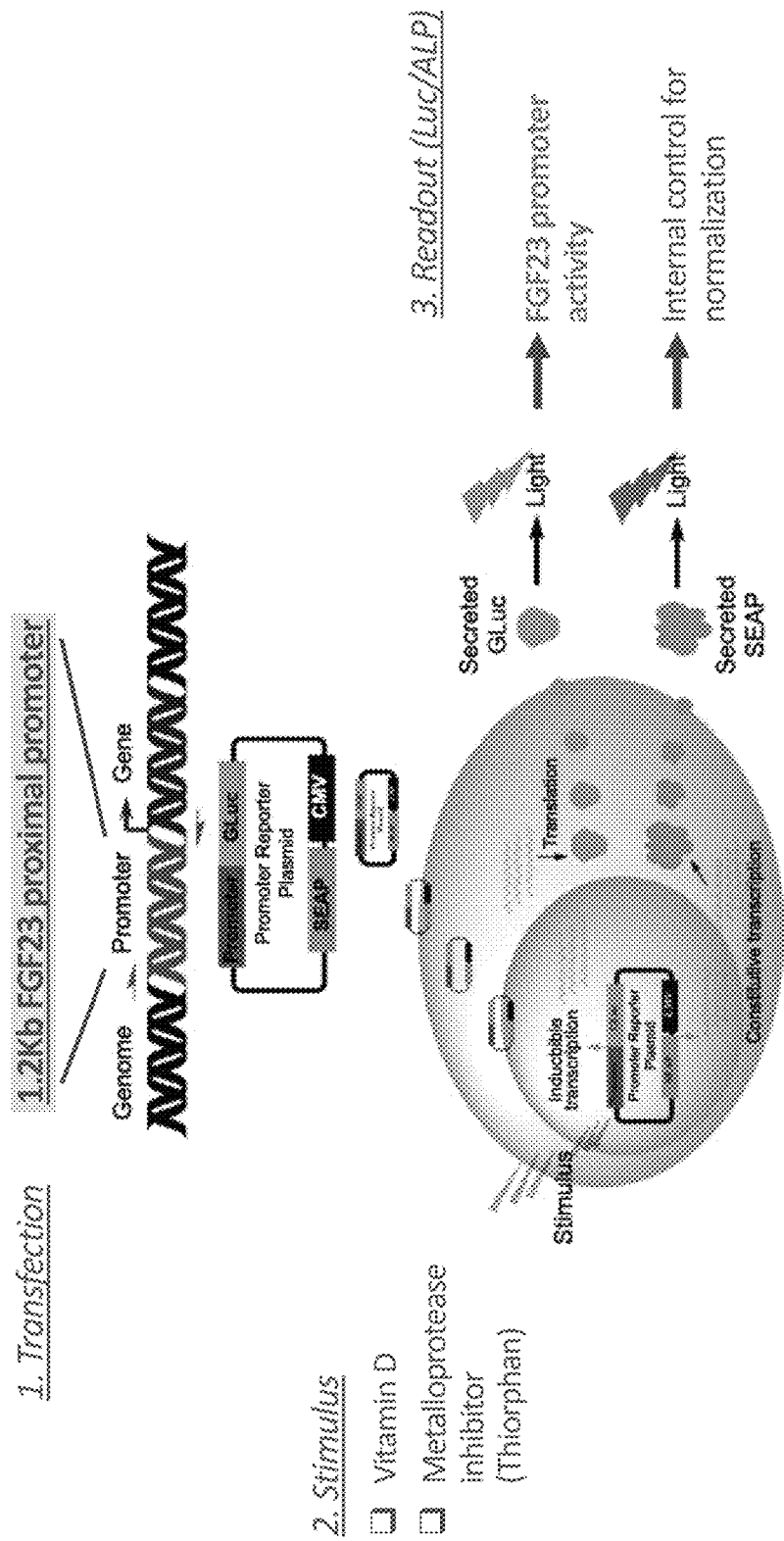
FIG. 14. MC3T3-E1 osteoblasts reporting FGF23 promoter activity.
Figure 15:
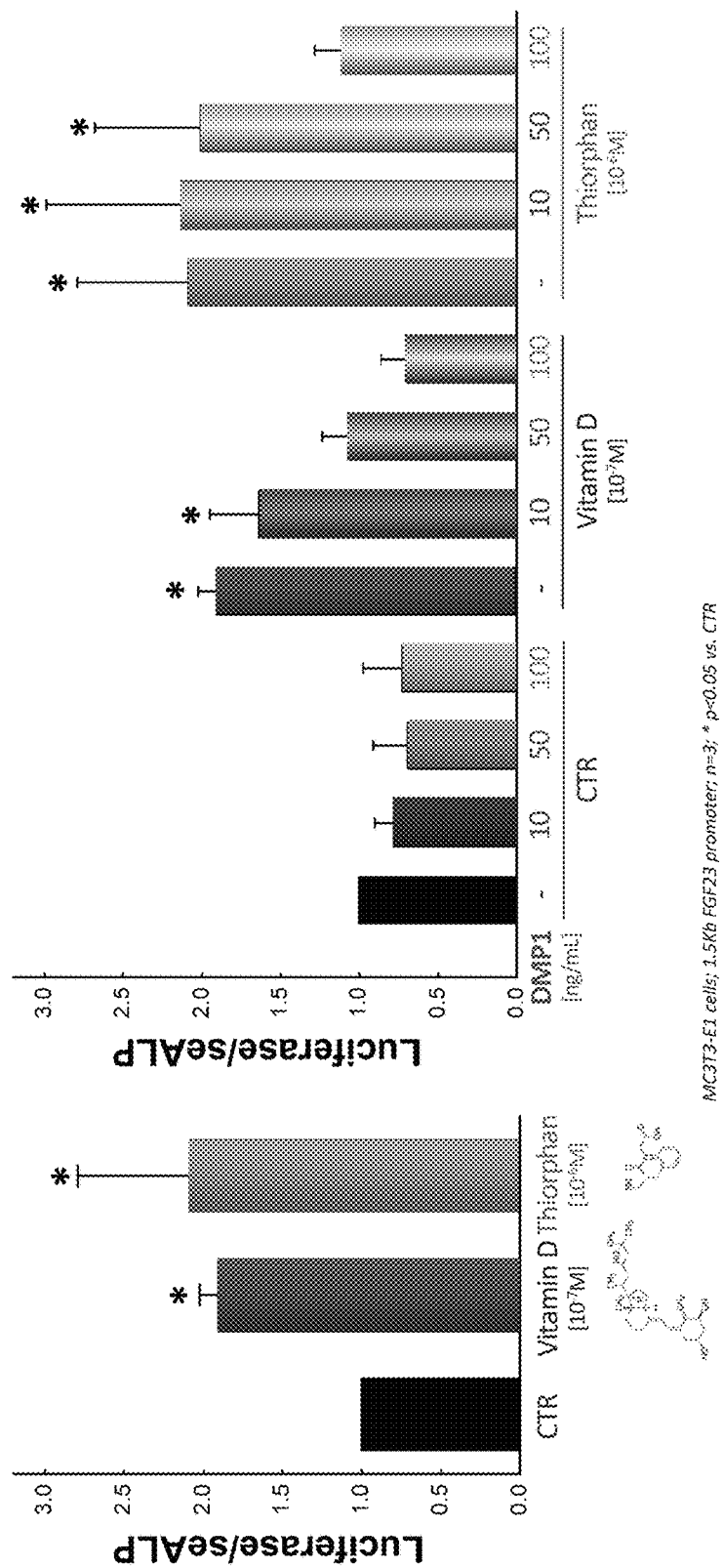
FIG. 15. PHEX inhibition blocks regulation of FGF23 promoter by DMP1.
Figure 16:
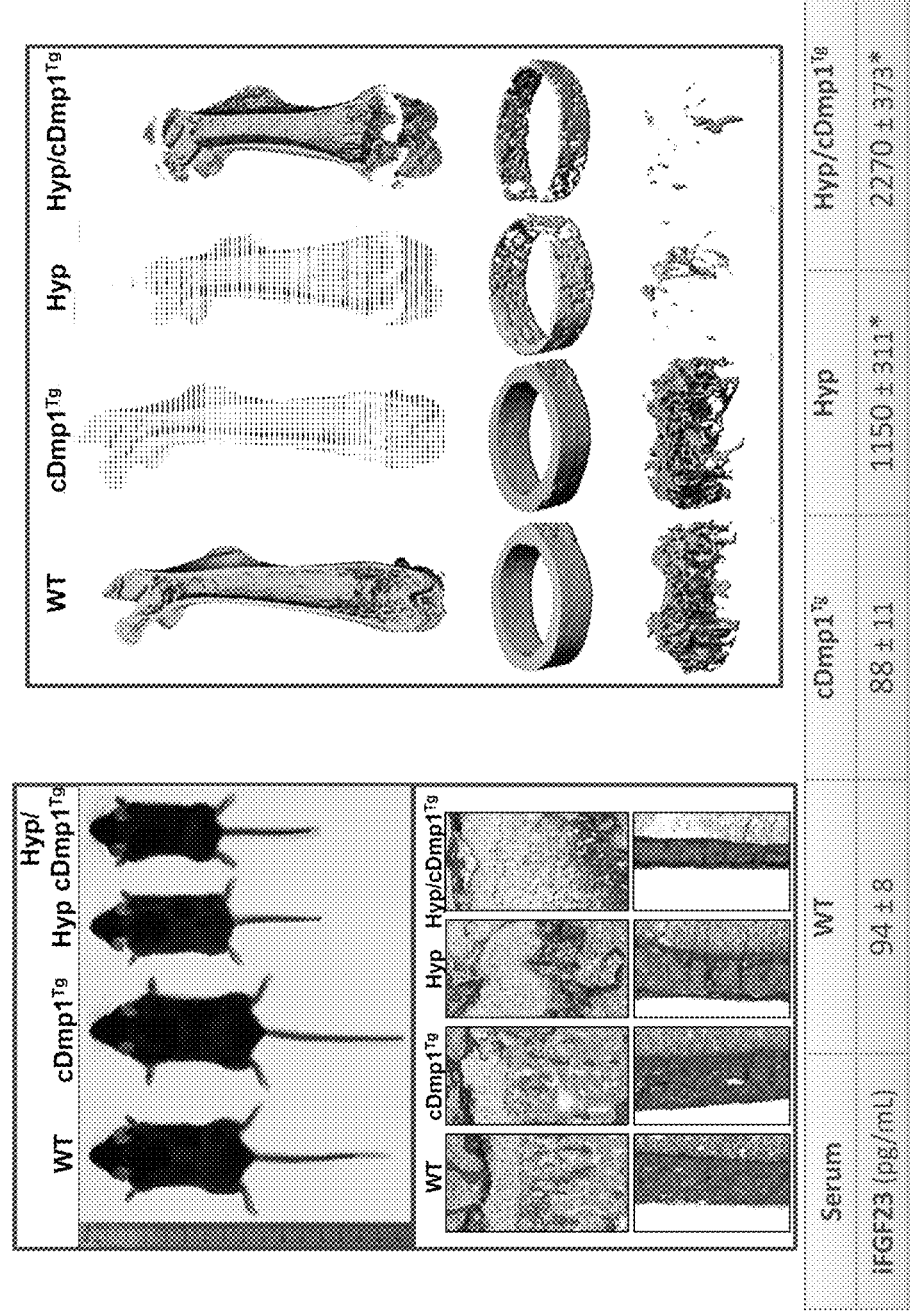
FIG. 16. cDMP1 mediates DMP1 function through PHEX.
Figure 17:
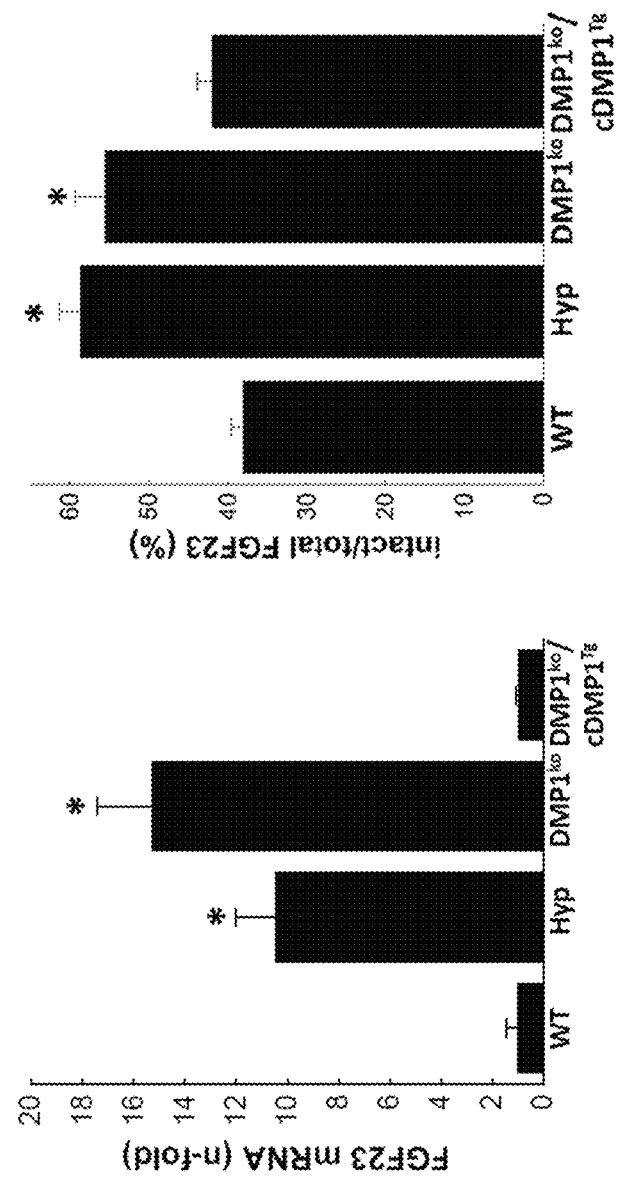
FIG. 17. cDMP1 regulates FGF23 transcription and cleavage.
Figure 18:
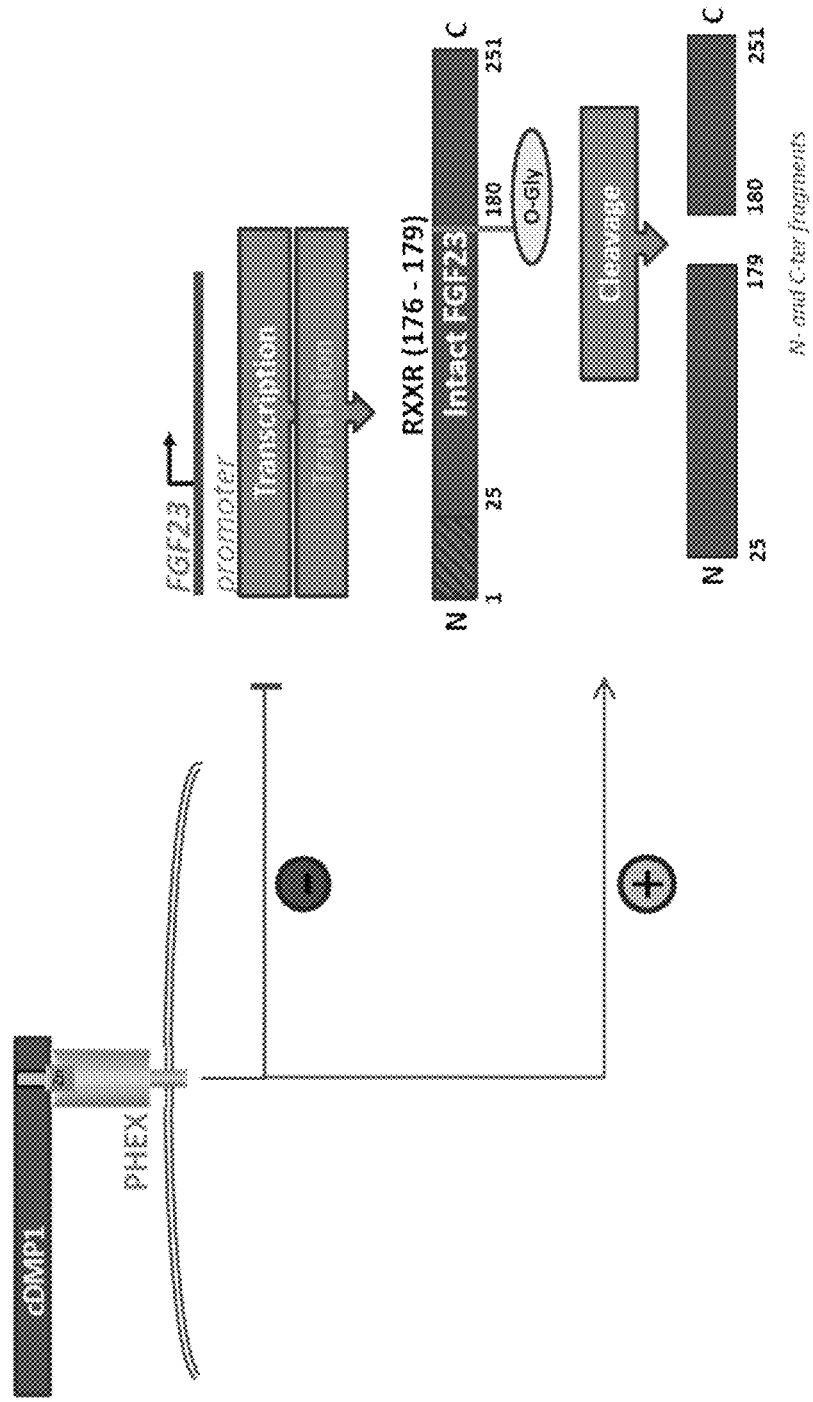
FIG. 18. Regulation of circulating FGF23 levels by cDMP1.
Figure 19:
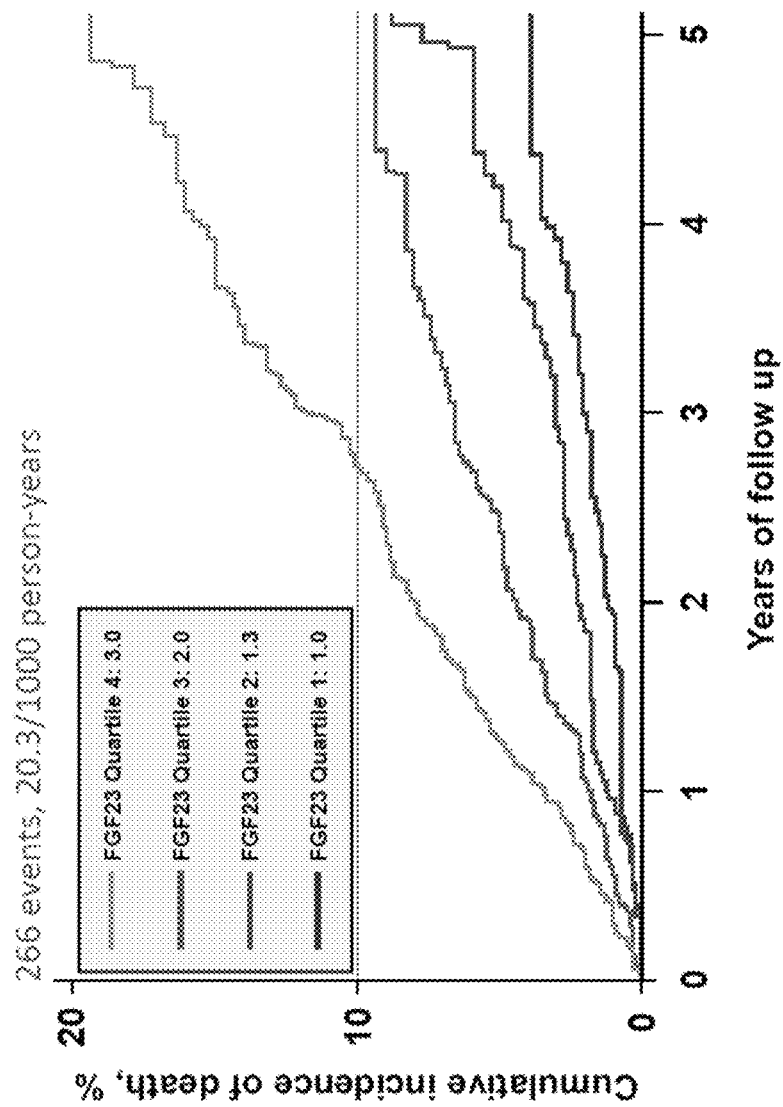
FIG. 19. FGF23 and mortality in CKD 2-4 patients.
Figure 20:
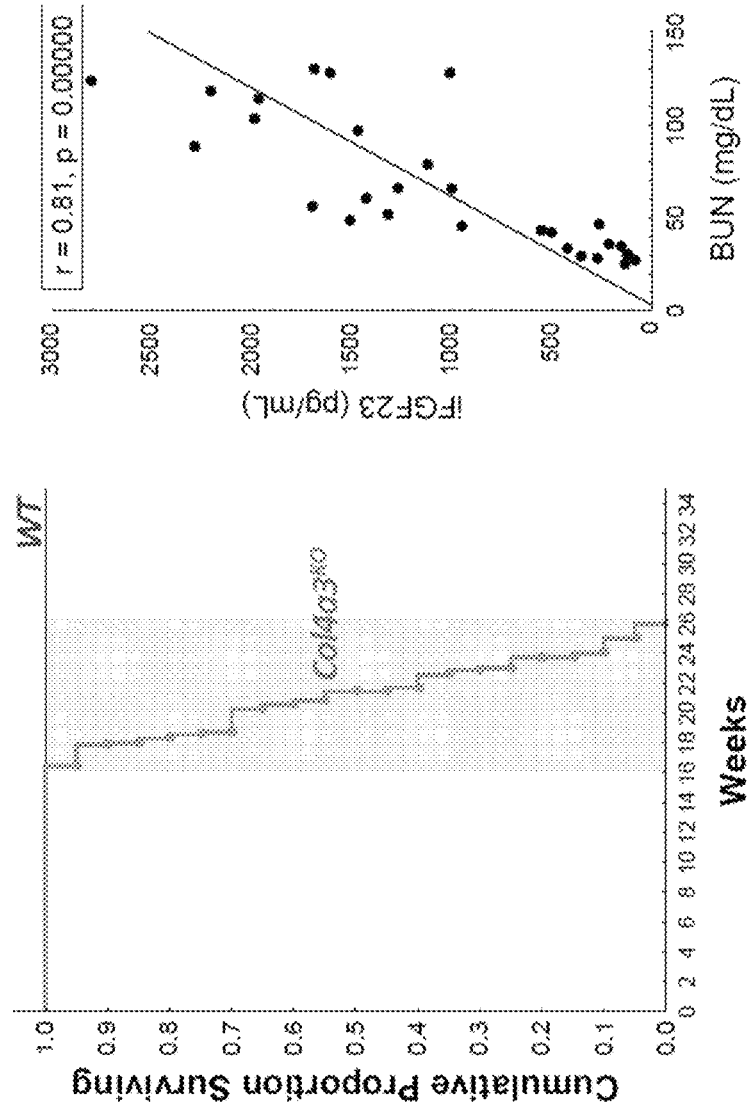
FIG. 20. FGF23 and mortality in Col4a3KO mice.
Figure 21:
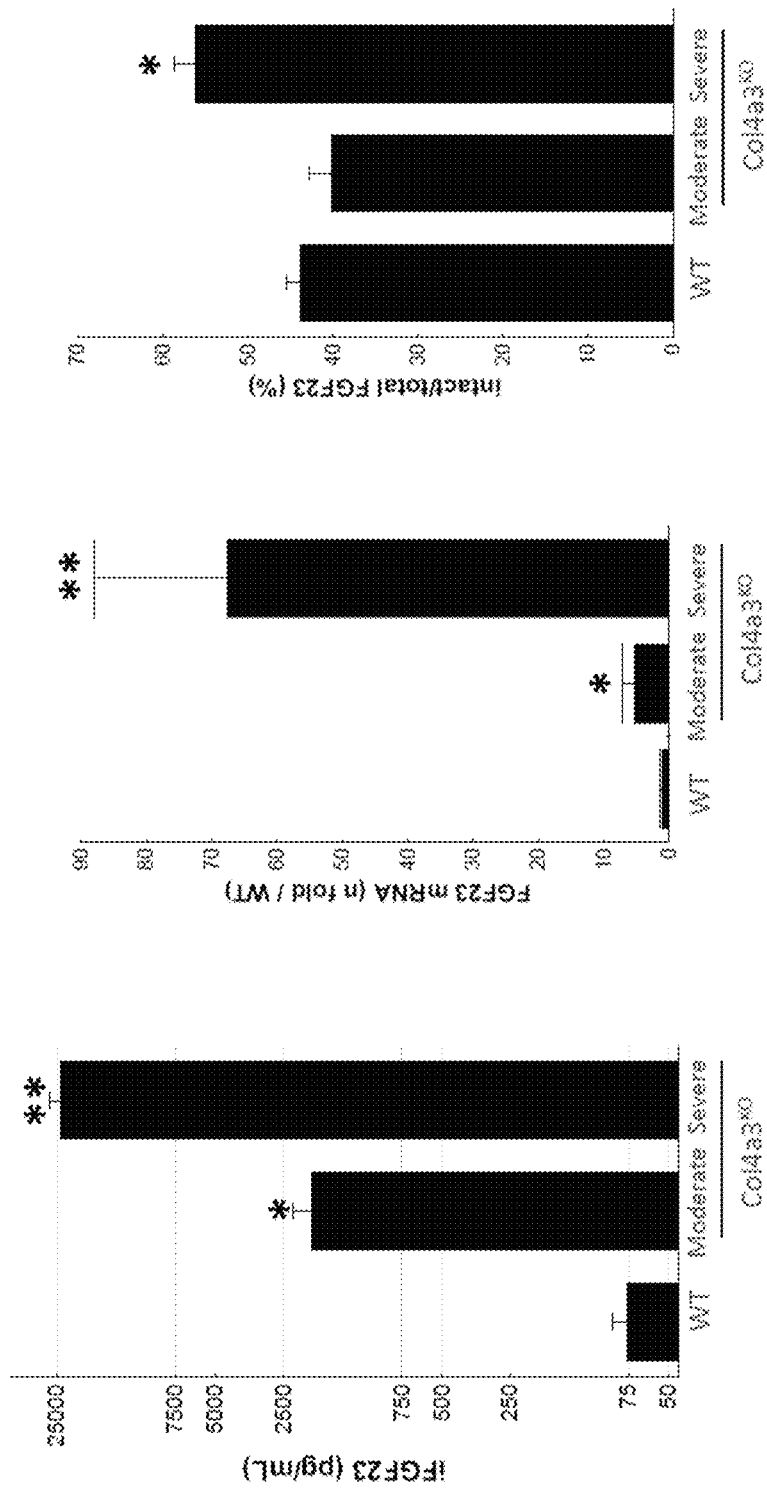
FIG. 21. Impaired production and cleavage of iFGF23 in CKD mice.
Figure 22:
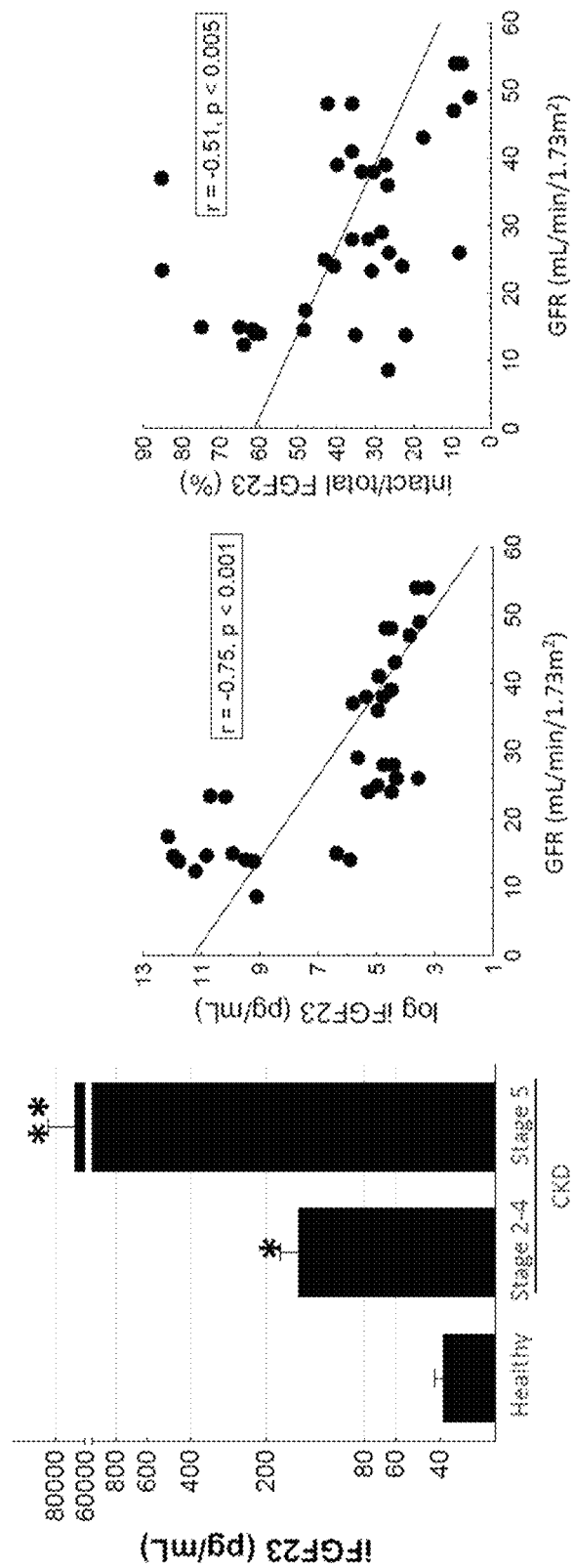
FIG. 22. Impaired production and cleavage of iFGF23 in CKD patients.
Figure 23:
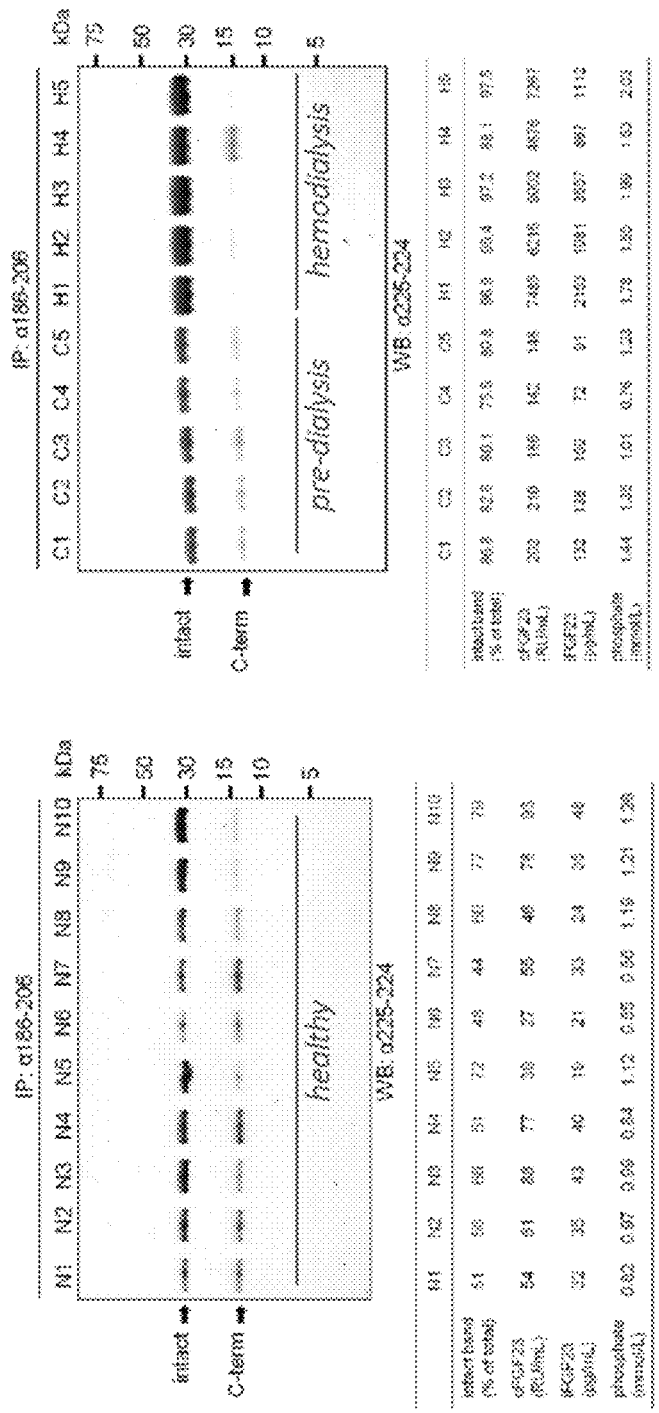
FIG. 23. Impaired production and cleavage of iFGF23 in CKD patients.
Figure 24:
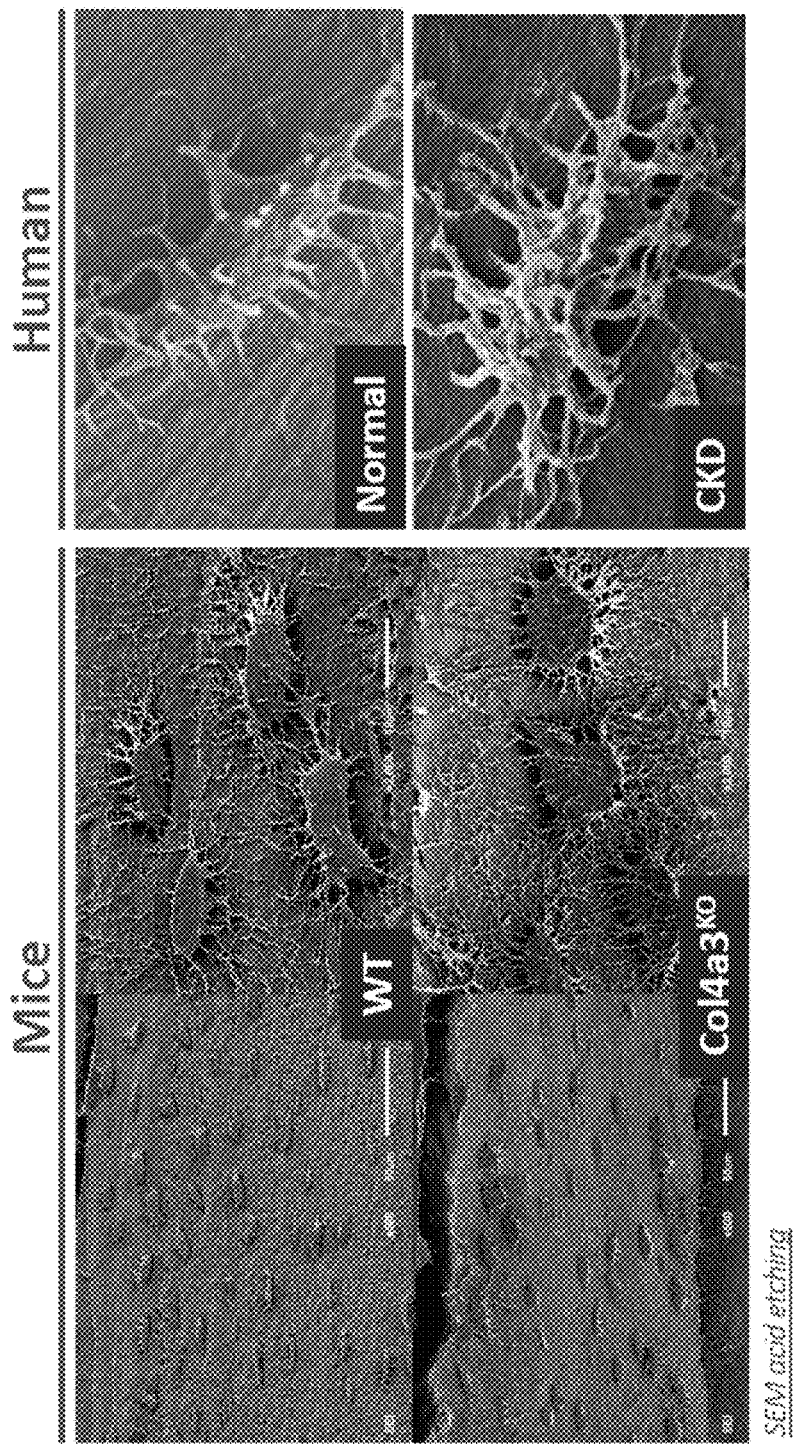
FIG. 24. Impaired osteocyte morphology in CKD mice and patients.
Figure 25:
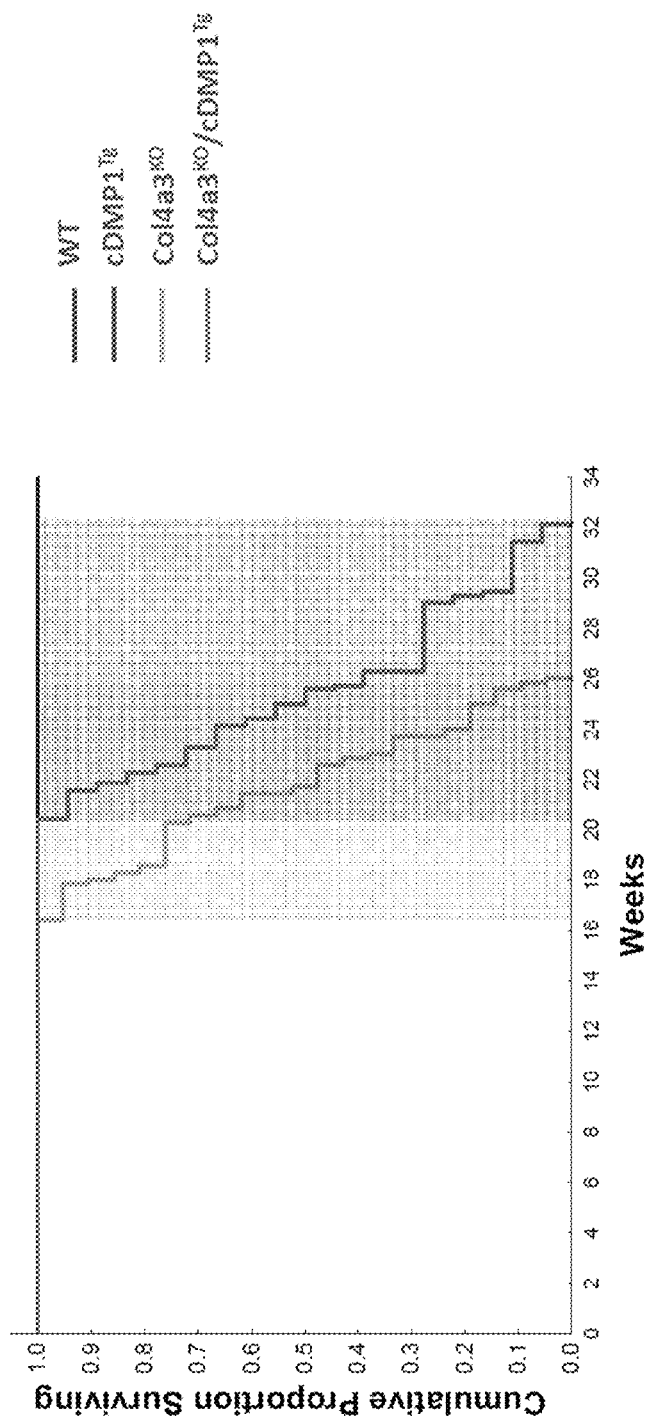
FIG. 25. cDMP1 improves survival in CKD. The lifespan of C57Bl6/J-Col4a3$^{KO}$ is typically 22 weeks. Overexpression of C-terminal DMP1 in the bone of Col4a3$^{KO}$ mice prevented elevation of circulating intact FGF23 levels, prevented cardiac hypertrophy and as a result prolonged the lifespan of CKD mice to about 26 weeks despite persistent alterations in renal function, blood pressure and mineral metabolism.

WT and Col4a3ko mice were injected with mouse rDMP1 (R&D Biosystems) daily for 1 week. Whole bone FITC staining (FIG. 10A) and Imaris modelisation technique (FIG. 10B) was used to quantify parameters of the osteocyte network. This technique allows quantitative analysis of osteocyte organization and morphology in stacked views of non-decalcified bone sections. Osteocyte organization and morphology was restored in Col4a3ko mice by DMP1 treatment, including size of osteocyte networks, shape and size of osteocytes, and length and number of their dendrites (FIG. 10C). Treatment of young Col4a3ko mice (moderate CKD) with DMP1 reduced iFGF23 levels by 30% while untreated Col4a3ko mice showed a 70% elevation during the same week (FIG. 11A). Treating older Col4a3ko mice (severe CKD) with DMP1 stabilized iFGF23, whereas levels continued to rise in untreated Col4a3ko mice (FIG. 11B).

DMP1 Injections:

recombinant mouse DMP1 (R&DSystems) was injected daily for 7 days to 5 week-old and 8 week-old WT and Col4a3KO mice on the [129X1/SvJ] genetic background (10 ng/g/d). Tissues were harvested post sacrifice on the 8th day, 24 hours after the last injection.

cDMP1 Bone Transgene Expression (cDMP1Tg-Col1a1 Promoter):

cDMP1Tg mice were provided on the [C57Bl6/J] genetic background and to keep maximum consistency between both strains Col4a3KO [129X1/SvJ] mice were derived and backcrossed onto [C57Bl6/J] mice for 4 generations to create Col4a3KO [C57Bl6/J] mice. Heterozygous Col4a3+/− females are then crossed with cDMP1Tg males to generate Col4a3+/−/cDMP1Tg mice. Col4a3+/−/cDMP1Tg males are crossed with Col4a3+/− females to generate four experimental groups: Col4a3+/+ (WT), Col4a3+/+/cDMP1Tg (cDMP1Tg), Col4a3−/− (Col4a3KO) and Col4a3−/−/cDMP1Tg (Col4a3KO/cDMP1Tg). Survival was first assessed in males and females from all groups. Tissues were then harvested on 20 week-old animals.

The invention claimed is:

1. A method comprising administering to a subject suffering from chronic kidney disease a composition comprising a dentin matrix protein 1 (DMP1) of SEQ ID NO: 1 or SEQ ID NO: 2.

2. The method of claim 1, wherein the subject exhibits above normal levels of circulating FGF23.

* * * * *